United States Patent [19]

Lukas et al.

[11] Patent Number: 5,189,017

[45] Date of Patent: Feb. 23, 1993

[54] USE OF SUGAR DERIVATIVES FOR THE PROPHYLAXIS AND TREATMENT OF VIRUS INFECTIONS

[75] Inventors: Bohumir Lukas, Basle; Karl H. Schmidt-Ruppin, Arlesheim, both of Switzerland

[73] Assignee: Ciba-Geigy Corporation, Ardsley, N.Y.

[21] Appl. No.: 601,600

[22] Filed: Oct. 17, 1990

Related U.S. Application Data

[63] Continuation of Ser. No. 319,909, Mar. 3, 1989, abandoned, which is a continuation of Ser. No. 750,667, Jul. 1, 1985, abandoned, which is a continuation of Ser. No. 640,547, Aug. 14, 1984, abandoned, which is a continuation of Ser. No. 515,006, Jul. 18, 1983, abandoned.

[30] Foreign Application Priority Data

Jul. 23, 1982 [CH] Switzerland ............ 4528/82

[51] Int. Cl.$^5$ ............................................. A61K 31/70
[52] U.S. Cl. ...................................... 514/8; 530/322; 514/23; 514/55.2; 536/18.7; 536/53; 536/55.2
[58] Field of Search ......................... 514/8; 530/322

[56] References Cited

U.S. PATENT DOCUMENTS

| | | | |
|---|---|---|---|
| 2,436,699 | 2/1948 | Rose | 260/403 |
| 2,447,715 | 8/1948 | Rose | 260/326 |
| 3,663,235 | 5/1972 | Menz et al. | 99/123 |
| 4,082,735 | 4/1978 | Jones et al. | 260/112.5 |
| 4,082,736 | 4/1978 | Jones et al. | 260/112.5 |
| 4,119,714 | 10/1978 | Kny et al. | 424/199 |
| 4,235,792 | 11/1980 | Hsia et al. | 260/403 |
| 4,254,115 | 3/1981 | Davidson et al. | 424/211 |
| 4,323,560 | 6/1982 | Baschang et al. | 424/177 |
| 4,372,949 | 2/1980 | Kodama et al. | 424/199 |
| 4,377,570 | 3/1983 | Durette et al. | 514/8 |
| 4,406,890 | 9/1983 | Tarcsay et al. | 514/8 |
| 4,414,204 | 12/1983 | Tarcsay et al. | 424/177 |
| 4,423,038 | 12/1983 | Baschang et al. | 260/112.5 R |
| 4,426,330 | 1/1984 | Sears | 260/403 |
| 4,426,525 | 1/1984 | Hozumi et al. | 546/22 |
| 4,493,832 | 1/1985 | Teraji et al. | 424/199 |
| 4,534,899 | 8/1985 | Sears | 260/403 |
| 4,548,923 | 10/1985 | Hartmann et al. | 514/8 |

FOREIGN PATENT DOCUMENTS

| | | |
|---|---|---|
| 0056992 | 2/1982 | European Pat. Off. |
| 72111 | 2/1983 | European Pat. Off. |
| 72286 | 2/1983 | European Pat. Off. |
| 2051069 | 1/1981 | United Kingdom |

OTHER PUBLICATIONS

The Merck manual of Diagnosis and Therapy, 5th ed., Pub. by Merck Sharp and Dohme Research Lab. (1987) pp. 158–186.
Stedman's Medical Dictionary, 23rd ed. 1976, p. 1554.
Lukas et al., Archives of Virology vol. 49 pp. 1–11 (1975).
Avery's Drug Treatment 3rd Ed. pp. 1230–1249 (1987).
Derwent Abstract of European 138558 (Apr. 1985).
Derwent Abstract of Japanese 52087221 (1977).
Journal of Immunological Methods vol. 65 pp. 295–306 (1983).
Chem. Abstr. 66:95388g (1967).
Chem. Abstr. 69:95890b (1968).
Chem. Abstr. 71:123473e (1969).

*Primary Examiner*—Johnnie R. Brown
*Assistant Examiner*—Elli Peselev
*Attorney, Agent, or Firm*—Irving M. Fishman; Karen G. Kaiser

[57] ABSTRACT

Described are the use of hexopyranose compounds of the formula I

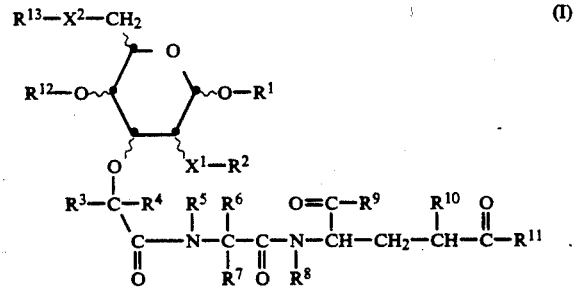

for the prophylaxis and treatment of virus infections, and novel pharmaceutical preparations especially suitable for the use in accordance with the invention.

The substituents in formula I have the meanings given in the claims.

9 Claims, 7 Drawing Sheets

USE OF SUGAR DERIVATIVES FOR THE PROPHYLAXIS AND TREATMENT OF VIRUS INFECTIONS

This application is a continuation of application Ser. No. 07/319,909 filed Mar. 3, 1989, now abandoned; which is a continuation of application Ser. No. 06/750,667 filed Jul. 1, 1985, now abandoned; which is a continuation of Ser. No. 06/640,547 filed Aug. 14, 1984, now abandoned; which is a continuation of Ser. No. 06/515,006 filed Jul. 18, 1983, now abandoned.

The present invention relates to the use of sugar derivatives, especially hexopyranose compounds of the formula I,

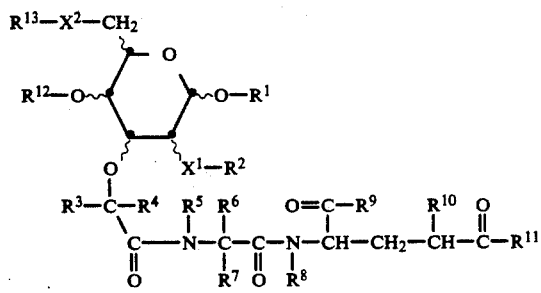

in which
each of $X^1$ and $X^2$, independently of the other, represents a group of the formula —O— or —N($R^{14}$)—, $R^{14}$ representing hydrogen or lower alkyl,
each of $R^1$, $R^2$, $R^{12}$ and $R^{13}$, independently of one another, represents a radical of the formula Ia

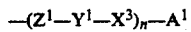

in which n represents 0 or 1, $Z^1$ represents carbonyl or thiocarbonyl, $Y^1$ represents unsubstituted or substituted alkylene which may be interrupted by iminocarbonyl or oxycarbonyl, $X^3$ represents a group of the formula —O— or —N($R^{14}$)—, wherein $R^{14}$ has the meaning given above, and $A^1$ represents a radical of the formula Ib,

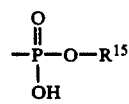

in which $R^{15}$ represents an aliphatic or cycloaliphatic radical having at least 7 carbon atoms, or $A^1$ represents a group of the formula Ic,

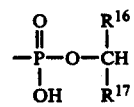

in which $R^{16}$ represents hydrogen and $R^{17}$ represents 2-hydroxyethyl or 1,2-dihydroxyethyl, wherein at least one hydroxy group is esterified or etherified by a radical having at least 7 carbon atoms, or in which each of $R^{16}$ and $R^{17}$, independently of the other, represents esterified or etherified hydroxymethyl, the esterifying or etherifying radicals having at least 7 carbon atoms, or each of $R^1$, $R^2$, $R^{12}$ and $R^{13}$, independently of one another, represents hydrogen, acyl other than a radical of the formula Ia in which n represents 1, or a radical that can be removed under physiological conditions,
each of $R^3$, $R^4$, $R^5$, $R^7$ and $R^8$, independently of one another, represents hydrogen or lower alkyl,
$R^6$ represents hydrogen or lower alkyl that is unsubstituted or substituted by a group of the formula Id, $$-E-(Z^2-Y^2-X^4)_m-A^2 \quad (Id)$$

in which m represents 0 or 1, E represents a group of the formula —O—, —S— or —N($R^{14}$)—, $R^{14}$ having the meaning given above, $Z^2$ represents carbonyl or thiocarbonyl, $Y^2$ represents unsubstituted or substituted alkylene which may be interrupted by iminocarbonyl or oxycarbonyl, $X^4$ represents a group of the formula —O— or —N($R^{14}$)—, $R^{14}$ having the meaning given above, and $A^2$ represents a radical of the formula Ib or Ic; or by free or etherified hydroxy or mercapto, by esterified hydroxy or mercapto other than a group of the formula Id, by free amino or substituted amino other than a group of the formula Id, by free, esterified or amidated carboxy, by cycloalkyl, by carbocyclic aryl or by nitrogen-containing heteroaryl having 5 or 6 ring members in the heterocyclic ring,
or
$R^5$ and $R^6$ together represent unsubstituted or substituted 1,3- or 1,4-lower alkylene,
each of $R^9$ and $R^{11}$, independently of the other, represents a radical of the formula Ie, $$-X^5-Y^3-X^6-A^3 \quad (Ie)$$

in which $X^5$ represents a group of the formula —O—, —S— or —N($R^{14}$)—, and $X^6$ represents a group of the formula —O— or —N($R^{14}$)—, in each case $R^{14}$ having the meaning given above, $Y^3$ represents unsubstituted or substituted alkylene which may be interrupted by iminocarbonyl or oxycarbonyl, and $A^3$ represents a radical of the formula Ib or Ic, or free hydroxy or mercapto, etherified hydroxy or mercapto other than a radical of the formula Ie, or free amino or substituted amino other than a radical of the formula Ie, and
$R^{10}$ represents hydrogen or free, esterified or amidated carboxy,
with the proviso that the compounds of the formula I have at least one radical $A^1$, $A^2$ or $A^3$, and the use of pharmaceutically acceptable salts of such compounds for the prophylaxis and (preferably) treatment of virus infections in warm-blooded animals, especially and including humans, and to novel pharmaceutical preparations that contain hexopyranose compounds of the formula I.

By contrast with the treatment of bacterial infections, agents available for the prophylaxis and treatment of virus infections are few and inadequate so that to overcome viral diseases it is in almost all cases necessary that the organism itself has adequate powers of defence.

In accordance with the invention it has surprisingly been found that the above-mentioned hexopyranose compounds of the formula I and their pharmaceutically acceptable salts are excellently suitable both for the prophylaxis and treatment of virus infections, as demonstrated, for example, by animal experiments such as those illustrated in the Examples. In these animal experiments animals, such as mice or guinea pigs, are infected by a wide variety of types of virus in a dose that is lethal for all or the large majority of untreated (control) animals, for example $LD_{80-90}$, and the course of the infection is observed in the untreated control animals compared with animals that are treated before, at the same time as, or after the infection, with one of the above-mentioned hexopyranose compounds or a salt thereof.

These experiments demonstrate that the antiviral action of the above-mentioned hexopyranose compounds of the formula I and their salts is not achieved by any hitherto known antiviral substance of any structure. It is especially remarkable that a prophylactic effect is produced when hexopyranose compounds of the formula I are administered from just a few days up to a few, for example four, weeks before infection, and a therapeutic effect still occurs on administration several days, for example 1 week, after infection.

Remarkable and hitherto unprecedented is also the broad viral spectrum against which the above-mentioned compounds are effective.

The hexopyranose compounds of the formula I can be used especially for the prophylaxis and treatment of diseases caused by the viruses specified in detail hereinafter [for nomenclature cf. J. L. Melnick, Prog. med. Virol. 26, 214–232 (1980) and 28, 208–221 (1982)]: DNA viruses with cubic symmetry and naked nucleocapsid, DNA viruses with enveloped virion and also RNA viruses with cubic, and those with helical, symmetry of the capsid.

Preferably, the compounds of the formula I are used in the case of DNA viruses with enveloped virion and cubic symmetry of the capsid, in the case of RNA viruses with cubic symmetry of the capsid and naked virion, and in the case of RNA viruses with helical symmetry of the capsid, in which the nucleocapsid casing is located at the surface membrane, but also in the case of Adenoviridae, Poxviridae and Coronaviridae, such as, especially, human coronaviruses.

The compounds of the formula I are used especially in the case of Herpesviridae, Picornaviridae and myxoviruses, but also in the case of mastadenoviruses, such as, especially, human adenoviruses, in the case of Chordopoxvirinae, such as, chiefly, orthopoxviruses, such as, especially, for example, vaccinal viruses, in the case of Reoviridae, chiefly (especially human) rotaviruses, and also in the case of Caliciviridae and Rhabdoviridae, such as, especially, vesiculoviruses in humans as well as horses, cows and pigs.

The compounds of the formula I are mainly used in the case of Alphaherpesvirinae like Varicellaviruses, for example human varicellazoster viruses, rhinoviruses, cardioviruses and Orthomyxoviridae, but also in the case of Betaherpesvirinae, such as, especially, human cytomegaloviruses, in the case of aphthoviruses, especially aphthoviruses of cloven-hoofed animals, such as, chiefly, cows, and in the case of Paramyxoviridae, such as, especially, pneumoviruses, for example respiratory syncytial viruses in humans, and such as, in addition, morbilliviruses or paramyxoviruses, such as parainfluenza viruses, for example human parainfluenza viruses, including Sendai viruses, as well as in the case of arboviruses or vesiculoviruses, for example vesicular stomatitis viruses.

Above all the compounds of the formula I are used for simplex viruses, for example human herpes simplex viruses of types 1 and 2, and in the case of human encephalomyocarditis viruses, influenza viruses, such as mainly influenza A and influenza B viruses, and most especially in the case of the viruses mentioned in the Examples.

The hexopyranose compounds of the formula I can be used in accordance with the invention by administering them enterally or parenterally, especially together with suitable adjuncts or carriers. Preferably they are applied to the mucous membrane, for example intranasally, rectally, vaginally or to the conjunctiva of the eye, or orally. The antiviral effect occurs, however, also if administered in other ways, for example subcutaneously, intravenously, intramuscularly or if applied to the skin.

The dosage of the active ingredient depends, inter alia, on the species of the warm-blooded animal, the defensive condition of the organism, the mode of administration and the nature of the virus. There is no especially pronounced relationship between dosage and action.

For prophylaxis, a single dose of from approximately 0.01 mg to approximately 25 mg, preferably from 0.05 to 7 mg, for example 0.5 mg, of active ingredient is administered to a warm-blooded animal of approximately 70 kg body weight, for example a human. The prophylactic effect of this dose lasts for several weeks. If required, for example at times of increased risk of infection, the administration of this dose can be repeated.

The therapeutic dose for warm-blooded animals of approximately 70 kg body weight is between 0.1 mg and 50 mg, preferably between 1 and 10 mg, for example 5 mg, especially when administered orally. The dosage in the case of topical, especially intranasal, administration is lower by up to a factor of 10. If required, the administration of the hexopyranose compounds of the formula I can be repeated until there is an improvement in the disease. Normally, however, one administration is adequate.

Preferably, the hexopyranose compounds of the formula I are used in accordance with the invention in the form of pharmaceutical preparations that contain a pharmacologically active amount of the active ingredient together with pharmaceutically acceptable carriers that are suitable for enteral, for example oral, or parenteral, administration and may be inorganic or organic, solid or liquid. For example, tablets or gelatin capsules that contain the active ingredient together with diluents, for example lactose, dextrose, sucrose, mannitol, sorbitol, cellulose and/or glycerin, and/or lubricants, for example siliceous earth, talc, stearic acid or salts thereof, such as magnesium or calcium stearate, and/or polyethylene glycol, are used. Tablets may likewise contain binders, for example magnesium aluminium silicate, starches, such as corn, wheat or rice starch, gelatin, methyl cellulose, sodium carboxymethyl cellulose and/or polyvinylpyrrolidone and, if desired, disintegrators, for example starches, agar, alginic acid or a salt thereof, such as sodium alginate, and/or effervescing mixtures, or adsorbents, colouring substances, flavouring substances and sweeteners. Furthermore, the pharmacologically active compounds of the present invention can be used in the form of parenterally administrable preparations, for example infusion solutions. Such solutions are preferably isotonic aqueous solutions or suspensions, and these, for example in the case of lyophilised preparations that contain the active ingredient alone or together with a carrier, for example mannitol, can be prepared before use. The pharmaceutical preparations may be sterilised and/or contain adjuncts, for example preservatives, stabilisers, wetting agents and/or emulsifiers, solubilisers, salts for regulating the osmotic pressure and/or buffers. The pharmaceutical preparations in question are produced in a manner known per se, for example by means of conventional mixing, granulating, confectioning, dissolving or lyophilising processes, and contain from approximately 0.001% up to approximately 95% of active ingredient, an active ingredient content of less than 1% being suitable especially for preparations that are to be topically administered.

Pharmaceutical preparations for enteral or parenteral administration that contain an effective amount, but less than 1% by weight, of a hexopyranose compound of the formula I or a salt thereof together with a significant amount of a pharmaceutical carrier, are novel and the invention relates also to these.

The invention relates especially to pharmaceutical preparations containing a hexopyranose compound of the formula I that is mentioned below as being preferred for the use in accordance with the invention.

The following forms of administration, which have not been prior-published, of hexopyranose compounds of the formula I are especially suitable for the use in accordance with the invention: creams, ointments, pastes or a gel with an active ingredient content of from 0.001% up to, but exclusive of, 1% by weight, principally of from 0.001% to 0.9%, especially from 0.01% to 0.1%, for example 0.05%, for example ointments for intranasal administration, vaginal or rectal suppositories or lipsticks, aqueous solutions having an active ingredient content of from 0.001% by weight up to, but exclusive of, 1% by weight, principally from 0.001% to 0.9%, especially from 0.05% to 0.5%, for example 0.1%, preferably isotonic, sterile and physiologically tolerable solutions, for example eye drops, preferably in disposable micro-containers, or sprays for use in the mouth or pharyngeal cavity, or tablets or capsules having an active ingredient content of from 0.1 up to, but exclusive of, 1% by weight, for example 0.9%.

The pharmaceutical preparations described in the Examples are especially suitable.

Creams are oil-in-water emulsions that contain more than 50% of water. There are used as oily base substances especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. There come into consideration as emulsifiers surface-active substances having predominantly hydrophilic properties, such as corresponding non-ionic emulsifiers, for example fatty acid esters of polyalcohols or ethylene oxide adducts thereof, such as polyglycerin fatty acid esters or polyoxyethylene sorbitan fatty acid esters (Tweens), also polyoxyethylene fatty alcohol ethers or fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or stearyl alcohol. Additives to the aqueous phase are, inter alia, agents that reduce the drying out of creams, for example polyalcohols, such as glycerin, sorbitol, propylene glycol and/or polyethylene glycols, and also preservatives, perfumes etc.

Ointments are water-in-oil emulsions that contain up to 70%, preferably from approximately 20% to approximately 50%, of water or aqueous phase. There come into consideration as fatty phase especially hydrocarbons, for example petroleum jelly, paraffin oil and/or hard paraffins, which, in order to improve the water-binding ability, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerin, propylene glycol, sorbitol and/or polyethylene glycol, as well as preservatives, perfumes etc.

Fatty ointments are anhydrous and contain as the base substance especially hydrocarbons, for example paraffin, petroleum jelly and/or liquid paraffins, also natural or partially synthetic fats, for example coconut fatty acid triglyceride, or preferably hardened oils, for example hydrogenated peanut or castor oil, and fatty acid partial esters of glycerin, for example glycerin mono- and di-stearate, as well as, for example, the fatty alcohols that increase water-absorbing ability, emulsifiers and/or additives mentioned in connection with the ointments.

Pastes are creams and ointments with secretion-absorbing powder constituents, such as metal oxides, for example titanium oxide or zinc oxide, and also talc and/or aluminium silicates, the purpose of which is to bind any moisture or secretions present.

Foams are administered from pressurized containers and are liquid oil-in-water emulsions in aerosol form, halogenated hydrocarbons, such as chlorofluoro-lower alkanes, for example dichlorodifluoromethane and dichlorotetrafluoroethane, being used as propellants. There are used as oily phase, inter alia, hydrocarbons, for example paraffin oil, fatty alcohols, for example cetyl alcohol, fatty acid esters, for example isopropyl myristate, and/or other waxes. There are used as emulsifiers, inter alia, mixtures of those having predominantly hydrophilic properties, such as polyoxyethylene sorbitan fatty acid esters (Tweens), and those having predominantly lipophilic properties, such as sorbitan fatty acid esters (Spans). In addition there are the customary additives, such as preservatives, etc.

Tinctures and solutions usually have an aqueous/ethanolic base substance to which there are added, inter alia, polyalcohols, for example glycerin, glycols and/or polyethylene glycol, as humectants for reducing evaporation, and fat-restoring substances, such as fatty acid esters with low polyethylene glycols, that is to say lipophilic substances soluble in aqueous mixture as a replacement for the fatty substances removed from the skin by the ethanol, and, if necessary, other adjuncts and additives.

The manufacture of the topically administrable pharmaceutical preparations is carried out in a manner known per se, for example by dissolving or suspending the active ingredient in the base substance, or in a portion thereof, if necessary. When processing the active ingredient in the form of a solution, it is usually dissolved in one of the two phases before emulsification; when processing in the form of a suspension it is mixed with a portion of the base substance after emulsification and then added to the remainder of the formulation.

The above terms used for the definition of the compounds of the formula I have, within the scope of this application, preferably the following meanings:

Acyl, for example as $R^1$, $R^2$, $R^{12}$ and $R^{13}$, is especially the acyl radical of an organic carboxylic acid, especially an aliphatic, but also a cycloaliphatic, cycloaliphatic-aliphatic, aromatic or araliphatic carboxylic acid, which may have, for example, up to 90 carbon atoms.

Aliphatic carboxylic acids are, inter alia, alkanecarboxylic acids that are unsubstituted or substituted, for example, by hydroxy or etherified or esterified hydroxy, such as lower alkoxy or lower alkanoyloxy, or by unsubstituted or substituted amino, such as lower alkylamino, di-lower alkylamino or acylamino, for example alkanoylamino, and corresponding alkene- or alkyne-carboxylic acids that may have one or more double or triple bonds. These acids may contain, for example, up to 90 carbon atoms, $R^2$ as the radical of an aliphatic carboxylic acid, in the case when $X^1$ represents a group of the formula $-N(R^{14})-$, preferably representing the acyl radical of an unsubstituted or hydroxy-substituted lower alkanecarboxylic acid.

Cycloaliphatic carboxylic acids may be monocyclic or polycyclic and as a cycloaliphatic radical contain monocyclic or polycyclic cycloalkyl that is unsubstituted or is substituted, for example by hydroxy, and corresponding cycloalkenyl.

In cycloaliphatic-aliphatic radicals, the cycloaliphatic moiety and the aliphatic moiety have the meanings given above; such radicals are especially monocyclic or polycyclic cycloalkyl-lower alkyl.

Aromatic and araliphatic carboxylic acids are, inter alia, benzoic or phenyl-lower alkanecarboxylic acids that are unsubstituted or substituted, for example by lower alkyl, hydroxy, lower alkoxy or halogen.

Groups that can be removed under physiological conditions are especially organic silyl groups, especially aliphatically substituted silyl groups, such as tri-lower alkylsilyl.

Substituents of alkylene, which is represented by the radicals $Y^1$, $Y^2$ and $Y^3$, are, inter alia, hydroxy, esterified or etherified hydroxy, such as acyloxy, for example lower alkanoyloxy, or lower alkoxy, amino or substituted amino, such as lower alkylamino, di-lower alkylamino or acylamino, for example lower alkanoylamino. In an alkylene radical that is interrupted by iminocarbonyl or oxycarbonyl, there may be one or more, for example two, such groups and these may be present as groups of the formula $-N(R^{14})-C(=O)-$ or $-O-C(=O)-$, and as groups of the formula $-C(=O)-N(R^{14})-$ or $-C(=O)-O-$, and $R^{14}$ has the meaning given above and preferably represents hydrogen. An alkylene radical formed by the groups $R^5$ and $R^6$ and having 3 or 4 carbon atoms in the chain may be substituted, for example by hydroxy, which may be acylated, for example by a group of the formula Ia.

An aliphatic radical having at least 7 carbon atoms that is the group $R^{15}$ or etherifies a hydroxy group in a radical $R^{16}$ or $R^{17}$ is especially a corresponding unsubstituted or substituted alkyl radical but may also represent a corresponding unsaturated radical, such as an unsubstituted or substituted alkenyl radical having one or more double bonds, such radicals having, for example, from 7 up to and including 90 carbon atoms, preferably from 7 up to and including 30 carbon atoms. Substituents of such aliphatic radicals are, for example, hydroxy, etherified or esterified hydroxy, such as lower alkoxy or lower alkanoyloxy and-or unsubstituted or substituted amino, such as lower alkylamino, di-lower alkylamino or alkanoylamino.

A corresponding cycloaliphatic radical that is the group $R^{15}$ or a radical etherifying a hydroxy group in a radical $R^{16}$ or $R^{17}$ is especially monocyclic or polycyclic cycloalkyl, or also corresponding cycloalkenyl, which may contain one or more double bonds. Such radicals contain at least 7, and preferably from 7 to 30, carbon atoms, and may, in addition, be substituted, for example by hydroxy, etherified or esterified hydroxy, such as lower alkoxy or lower alkanoyloxy, or by unsubstituted or substituted amino, such as lower alkylamino, di-lower alkylamino or alkanoylamino.

Etherified hydroxy or substituted amino as a radical $R^9$ or $R^{11}$ is, for example, lower alkoxy, or, for example, lower alkylamino, in which lower alkyl may be substituted.

A radical esterifying a hydroxy group in a radical $R^{16}$ or $R^{17}$ is especially an acyl radical of an organic carboxylic acid, especially of one of the above-mentioned aliphatic and cycloaliphatic, cycloaliphaticaliphatic, aromatic or araliphatic, carboxylic acids, preferably having from 7 to 90 carbon atoms.

Etherified hydroxy or mercapto or esterified hydroxy or mercapto other than a radical of the formula Id as substituent of lower alkyl $R^6$ is, for example, lower alkoxy, acyloxy, such as alkanoyloxy, wherein alkanoyl contains up to 90, for example from 7 to 30, carbon atoms and may optionally be substituted, for example by hydroxy, or is halogen, lower alkylthio or acylthio, such as alkanoylthio, wherein alkanoyl contains up to 90, for example from 7 to 30, carbon atoms. Substituted amino other than a radical of the formula Id as substituent of a lower alkyl group $R^6$ is, for example, lower alkylamino, guanylamino or acylamino, such as alkanoylamino, wherein alkanoyl may contain up to 90, for example up to 30, carbon atoms. Esterified carboxy as substituent of a lower alkyl radical $R^6$ is preferably carboxy esterified by an aliphatic radical, such as alkyl having up to 30 carbon atoms, that is to say, for example, corresponding alkoxycarbonyl, whilst corresponding amidated carboxy, is, for example, aminocarbonyl or lower alkylaminocarbonyl, wherein lower alkyl may be substituted, for example by carboxy, alkoxycarbonyl or aminocarbonyl. Esterified or amidated carboxy in a radical $R^6$ may also be a radical of the formula

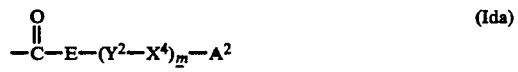

$$-\overset{O}{\underset{\|}{C}}-E-(Y^2-X^4)_m-A^2 \qquad (Ida)$$

in which m, E, $Y^2$, $X^4$ and $A^2$ have the meanings given above.

Aryl as substituent of a lower alkyl group $R^6$ is especially phenyl that is unsubstituted or substituted, for example by lower alkyl, hydroxy or etherified or esterified hydroxy, such as lower alkoxy, or halogen, whilst nitrogen-containing heteroaryl having 5 or 6 ring members in the heterocyclic ring as corresponding substituent of $R^6$ is monocyclic or bicyclic heteroaryl containing one or two nitrogen atoms as ring members.

Etherified mercapto as radical $R^9$ or $R^{11}$ is especially lower alkylthio, whilst in a lower alkylamino radical $R^9$ or $R^{11}$ the lower alkyl group may be substituted, for example by carboxy, lower alkoxycarbonyl or aminocarbonyl.

Esterified carboxy $R^{10}$ is especially lower alkoxycarbonyl, whilst amidated carboxyl $R^{10}$ may be carbamoyl or N-lower alkylcarbamoyl, wherein lower alkyl may be substituted, for example by carboxy, lower alkoxycarbonyl or aminocarbonyl.

In the context of the present description, the general terms used above have the following meanings, radicals and compounds that are termed "lower" containing up to and including 7, preferably up to and including 4, carbon atoms:

Alkyl is, for example, lower alkyl, such as methyl, ethyl, n-propyl, isopropyl, n-butyl, tributyl, sec.-butyl or tert.-butyl, also n-pentyl, neopentyl, n-hexyl or n-heptyl, or higher alkyl, such as straight-chain or branched octyl, nonyl, decyl, undecyl, dodecyl, tridecyl, tetradecyl, pentadecyl, hexadecyl, heptadecyl, nonadecyl or heneicosyl, and also higher alkyl of the triacontyl, tetracontyl, pentacontyl, hexacontyl, heptacontyl, octacontyl or nonacontyl series.

Lower alkoxy is, for example, methoxy, ethoxy, n-propoxy, isopropoxy, n-butoxy, isobutoxy or tert.-butoxy.

Alkanoyloxy is lower or higher alkanoyloxy, lower alkanoyloxy being, for example, formyloxy, acetoxy, propionyloxy or butyryloxy, whilst higher alkanoyloxy is, for example, lauroyloxy, myristinoyloxy, palmitoyloxy, stearoyloxy or behenoyloxy. Alkanoyloxy substituted by hydroxy, for example higher alkanoyloxy, is, inter alia, mycoloyloxy.

Lower alkylamino is, for example, methylamino, ethylamino, n-propylamino or isopropylamino. Di-lower alkylamino is, for example, dimethylamino, diethylamino or di-isopropylamino. Alkanoylamino is lower alkanoylamino, for example formylamino, acetylamino or propionylamino, or higher alkanoylamino, for example lauroylamino, palmitoylamino, stearoylamino or behenoylamino.

An alkanecarboxylic acid is, for example, a lower alkanecarboxylic acid, such as acetic acid, propionic acid, butyric acid or caproic acid, or a higher alkanecarboxylic acid, such as lauric acid, myristic acid, palmitic acid, stearic acid or behenic acid, whilst, for example, an alkanoic acid substituted by hydroxy may be, inter alia, mycolic acid.

Alkene- and alkyne-carboxylic acids are, inter alia, lower alkene- and lower alkyne-carboxylic acids, such as acrylic acid, crotonic acid or tetrolic acid, or higher alkene- and higher alkyne-carboxylic acids, such as undecylenic acid, oleic acid or elaidic acid. The acyl radical of a lower alkanecarboxylic acid, which is the group $R^2$ in the case when $X^1$ represents the radical of the formula $-N(R^{14})-$, is especially acetyl or hydroxyacetyl, and propionyl.

Cycloalkyl is, for example, cyclopentyl, cyclohexyl or adamantyl, whilst cycloalkenyl may be, for example, 1-cyclohexenyl, and cycloalkyl-lower alkyl may be, for example, 3-cholanylmethyl or the acyl radical of cholanic acid.

Phenyl-lower alkanecarboxylic acids are, for example, phenylacetic acid or phenylpropionic acid, which may be substituted, for example as stated.

Halogen is preferably halogen having an atomic number of up to 35 and represents especially chlorine, but also fluorine or bromine.

Tri-lower alkylsilyl is especially trimethylsilyl.

Alkylene is straight-chain or branched and is especially lower alkylene, for example methylene, ethylene, 1,2-propylene, 1,3-propylene or 1,6-hexylene, but also higher alkylene, such as 1,11-undecylene.

Alkenyl is lower alkenyl, for example allyl or methallyl, or higher alkenyl, for example decenyl.

Lower alkylthio is, for example, methylthio or ethylthio.

In an alkanoylthio radical, the alkanoyl radical represents lower alkanoyl, for example acetyl, propionyl, butyryl or hexanoyl, but may also represent higher alkanoyl, for example lauroyl, myristinoyl, palmitoyl, stearoyl or behenoyl.

Alkoxycarbonyl is lower alkoxycarbonyl, for example methoxycarbonyl, ethoxycarbonyl or tert.-butoxycarbonyl, or higher alkoxycarbonyl, for example dodecyloxycarbonyl, tetradecyloxycarbonyl, hexadecyloxycarbonyl or heneicosyloxycarbonyl.

Lower alkylaminocarbonyl is, for example, methylaminocarbonyl or ethylaminocarbonyl, also carboxy-, lower alkoxycarbonyl- or carbamoyl-lower alkylaminocarbonyl, such as carboxymethylaminocarbonyl, 1-carboxyethylaminocarbonyl, methoxycarbonylmethylaminocarbonyl or carbamoylmethylaminocarbonyl.

Nitrogen-containing heteroaryl having 5 or 6 ring members in the heterocyclic ring is, for example, imidazolyl, such as 4-imidazolyl, or indolyl, such as 3-indolyl.

The hexopyranose compounds of the formula I may be in the form of isomeric mixtures or pure isomers. They may thus have the L- or DL-configuration in the sugar moiety, but have preferably the D-configuration. Furthermore, the hexopyranose moiety may be that of any hexose, but is preferably that of an allose, galactose or mannose, but especially of a glucose. That is to say, the compounds of the present invention are especially corresponding allo-, galacto- or mannopyranose compounds, but more especially corresponding glucopyranose compounds, having preferably the D-configuration.

The radical of the formula $-C(R^3)(R^4)-C(=O)-$ linked to the oxygen atom, in the case where one of the groups $R^3$ and $R^4$ is other than hydrogen, is preferably in optically active form and has especially the D-configuration, whilst the radical of the amino acid of the formula $-N(R^5)-C(R^6)(R^7)-C(=O)-$, in the case where one of the radicals $R^6$ and $R^7$ is other than hydrogen, is likewise preferably in optically active form, especially in the L-configuration, and the terminal α-aminoglutaric acid radical is preferably in optically active form, especially in the D-configuration. Furthermore, the optionally substituted 1-hydroxy group of the formula $-O-R^1$ may have the α- or the β-configuration; the novel compounds of the formula I may, however, also be in the form of a mixture of the 1-α-and 1-β-isomers.

In the compounds of the formula I, the proton bonded to phosphorus via an oxygen atom can readily be replaced by a cation, that is to say, the compounds form salts. In this case, the compounds of the formula I may be in salt form or in the form of a mixture of the free compounds and their salts. These are especially metal or ammonium salts, such as alkali metal and alkaline earth metal salts, for example sodium, potassium, magnesium or calcium salts, and ammonium salts, or salts with suitable organic amines, such as lower alkylamines, for example triethylamine. Compounds of the formula I having basic groups, for example amino groups, are in the form of internal salts but, when there are more basic than acidic groups in a molecule of the formula I, they may also form acid addition salts with external acids, such as salts with inorganic acids, such as mineral acids, for example hydrochloric, sulphuric or phosphoric acid, or organic carboxylic or sulphonic acids, for example acetic, maleic, fumaric, tartaric, citric, methanesulphonic or 4-toluenesulphonic acid. Only the pharmaceutically acceptable, non-toxic salts are used therapeutically.

The above-mentioned hexopyranose compounds of the formula I and their salts and their preparation are described in the European Patent Applications with the publication numbers 0025 495, 0027 258 and 0056 992, which are in the name of the assignee of the present invention, and the last-mentioned Application was not published until after the priority data of the present Application. The use in accordance with the invention of the phosphorylmuramyl peptides per se for the prophylaxis and treatment of virus infections is neither described in, nor made obvious by, the above-mentioned Applications. The penultimate paragraph on page 13 of the above-mentioned application 0025 495 relates merely to their use as adjuvant in admixture with vaccines.

The present invention relates especially to the use of:

(a) compounds of the formula I in which $X^1$ and $X^2$ have the meanings given above, $R^1$ represents a radical of the formula Ia in which n, $Z^1$, $Y^1$, $X^3$ and $A^1$ have the meanings given above, each of $R^2$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id or by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, and of pharmaceutically acceptable salts of such compounds;

(b) compounds of the formula I in which $X^1$ and $X^2$ have the meanings given above, $R^2$ represents a radical of the formula Ia in which n, $Z^1$, $Y^1$, $X^3$ and $A^1$ have the meanings given above, each of $R^1$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted 1,3- or 1,4-lower alkylene, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, and of pharmaceutically acceptable salts of such compounds;

(c) compounds of the formula I in which $X^1$ and $X^2$ have the meanings given above, $R^{13}$ represents a radical of the formula Ia in which n, $Z^1$, $Y^1$, $X^3$ and $A^1$ have the meanings given above, each of $R^1$, $R^2$ and $R^{12}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents hydrogen or lower alkyl that is unsubstituted or substituted by free or etherified hydroxy or mercapto, by esterified hydroxy or mercapto other than a corresponding group of the formula Id, by free amino or substituted amino other than a corresponding group of the formula Id, by free, esterified or amidated carboxy, by cycloalkyl, by carbocyclic aryl or by nitrogen-containing heteroaryl having 5 or 6 ring members in the heterocyclic ring, or $R^5$ and $R^6$ together represent unsubstituted or substituted lower alkylene having 3 or 4 carbon atoms in the chain, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, and of pharmaceutically acceptable salts of such compounds; or (d) compounds of the formula I in which $X^1$ and $X^2$ have the meanings given above, each of $R^1$, $R^2$, $R^{12}$ and $R^{13}$, independently of one another, represents hydrogen, acyl other than a radical of the formula Ia in which n represents 1, or a group that can be removed under physiological conditions, $R^3$, $R^4$, $R^5$, $R^7$, $R^8$ and $R^{10}$ have the meanings given above, $R^6$ represents lower alkyl substituted by a radical of the formula Id, in which m, E, $Z^2$, $Y^2$, $X^4$ and $A^2$ have the meanings given above, or $R^6$ represents lower alkyl substituted by a group of the formula Ida in which m, E, $Y^2$, $X^4$ and $A^2$ have the meanings given above, and in which each of $R^9$ and $R^{11}$, independently of the other, represents free hydroxy or mercapto, etherified hydroxy or mercapto other than a radical of the formula Ie, or free amino or substituted amino other than a radical of the formula Ie, it being possible for free functional groups to be in protected form, and of pharmaceutically acceptable salts of such compounds, and to novel pharmaceutical preparations containing these compounds.

The invention includes especially the use of hexopyranose compounds, particularly D-glucopyranose compounds of the formula I, in which $X^1$ and $X^2$ have the meanings given above, each of $R^1$, $R^2$, $R^{12}$ and $R^{13}$, independently of one another, represents hydrogen, the acyl radical of an aliphatic, cycloaliphatic, aromatic or araliphatic carboxylic acid, especially of an alkanecarboxylic acid having up to 90 carbon atoms that is unsubstituted or substituted, for example by hydroxy, amino and/or alkanoylamino, such as higher alkanoylamino, a tri-lower alkylsilyl group or a radical of the formula Ia in which n and $X^3$ have the meanings given above, $Z^1$ represents thiocarbonyl or, preferably, carbonyl, $Y^1$ represents lower alkylene which may be interrupted by iminocarbonyl or oxycarbonyl, and $A^1$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, $R^3$, $R^4$, $R^5$, $R^7$ and $R^8$ have the meanings given above, $R^6$ represents hydrogen or lower alkyl which is unsubstituted or substituted by a radical of the formula Id in which m, E and $X^4$ have the meanings given above, $Z^2$ represents thiocarbonyl or, especially, carbonyl, $Y^2$ represents lower alkylene which may be interrupted by iminocarbonyl or oxycarbonyl, and $A^2$ represents a radical of the formula Ib or Ic in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is esterified by an aliphatic radical having at least 7 and up to 90 carbon atoms or by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, or $R^6$ represents lower alkyl substituted by hydroxy or mercapto, by hydroxy or mercapto etherified by an aliphatic radical containing up to 90 carbon atoms, by hydroxy or mercapto that is esterified by an aliphatic acyl radical containing up to 90 carbon atoms and is other than the group of the formula Id, by amino, by amino that is substituted by an acyl radical containing up to 90 carbon atoms and is other than a radical of the formula Id, by free carboxy, by lower alkoxycarbonyl, by carbamoyl, by lower alkylaminocarbonyl, by carboxy-lower alkylaminocarbonyl or by amidated carboxyl of the formula Ida, by phenyl that is unsubstituted or substituted by hydroxy, lower alkoxy or halogen, or by imidazolyl or indolyl, or $R^5$ and $R^6$ together represent 1,3- or 1,4-lower alkylene, each of $R^9$ and $R^{11}$, independently of the other, represents hydroxy, lower alkoxy, amino, lower alkylamino, carboxy-lower alkylamino, or a radical of the formula Ie, in which $X^5$ and $X^6$ have the meanings given above, $Y^3$ represents lower alkylene which may be interrupted by iminocarbonyl or oxycarbonyl, and $A^3$ represents a radical of the formula Ib or Ic, in which $R^{15}$ represents an aliphatic radical having at least 7 carbon atoms, $R^{16}$ represents hydrogen and $R^{17}$ represents 2-hydroxyethyl or 1,2-dihydroxyethyl, in which at least one hydroxy group is etherified by an aliphatic radical having at least 7 and up to 90 carbon atoms or is esterified by a corresponding aliphatic acyl radical, or each of $R^{16}$ and $R^{17}$, independently of the other, represents hydroxymethyl etherified by an aliphatic radical having at least 7 and up to 90 carbon atoms or esterified by a corresponding aliphatic acyl radical, and $R^{10}$ represents hydrogen, carboxy, lower alkoxycarbonyl, carbamoyl, lower alkylaminocarbonyl or carboxy-lower alkylaminocarbonyl, it being possible for free functional groups to be in protected form, with the proviso that the compounds of the formula I have at least one radical $A^1$, $A^2$ or $A^3$, and of pharmaceutically acceptable salts of such compounds, and to novel pharmaceutical preparations containing these compounds.

The invention relates especially to (e) the use of the hexapyranose compounds mentioned under (a), (b), (c) and (d), especially D-glucopyranose compounds of the formula I in which one, several or all of the radicals $X^1$, $X^2$, $R^1$, $R^2$, $R^3$, $R^4$, $R^5$, $R^6$, $R^7$, $R^8$, $R^9$, $R^{10}$, $R^{11}$, $R^{12}$ and $R^{13}$ have the meanings given in the preceding paragraphs, and of pharmaceutically acceptable salts of such compounds.

The invention relates more especially to (f) the use of D-glucopyranose compounds of the formula If $$R_a^{13}-O-CH_2 \quad (If)$$

(structural formula)

in which $R_a^1$ represents hydrogen, lower alkanoyl or a group of the formula Ia in which n represents 1, $Z^1$ represents carbonyl, $Y^1$ represents lower alkylene which may be interrupted by iminocarbonyl, $X^3$ represents a group of the formula —O— or —NH—, and $A^1$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms or is esterified by an alkanoyl radical having from 7 to 90 carbon atoms that is unsubstituted or substituted by hydroxy, amino and/or alkanoylamino having up to 30 carbon atoms, $R_a^2$ represents lower alkanoyl, hydroxy-lower alkanoyl, benzoyl or a group of the formula Ia, in which n, $Z^1$, $Y^1$, $X^3$ and $A^1$ have the meanings given above, $R_a^{12}$ represents hydrogen or lower alkanoyl, $R_a^{13}$ represents hydrogen, alkanoyl or hydroxyalkanoyl having up to 90 carbon atoms, alkanoylaminoalkanoyl having up to 30 carbon atoms or a group of the formula Ia in which n, $Z^1$, $Y^1$, $X^3$ and $A^1$ have the meanings given above, $R_a^3$ and $R_a^7$ represent hydrogen or methyl, $R_a^6$ represents hydrogen or lower alkyl that is unsubstituted or substituted by free hydroxy or mercapto, lower alkoxy, lower alkylthio, alkanoyloxy or hydroxyalkanoyloxy having up to 90 carbon atoms, phenyl, imidazolyl, indolyl or by a group of the formula Id, in which m represents 1, E represents a group of the formula —O— or —S—, $Z^2$ represents carbonyl, $Y^2$ represents lower alkylene which may be interrupted by iminocarbonyl, $X^4$ represents a group of the formula —O—, and $A^2$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, and each of the radicals $R_a^9$ and $R_a^{11}$, independently of the other, represents hydroxy, lower alkoxy, amino, lower alkylamino, carboxy-lower alkylamino or a radical of the formula Ie in which $X^5$ represents a group of the formula —O— or —NH—, $Y^3$ represents lower alkylene which may be interrupted by iminocarbonyl, $X^6$ represents a group of the formula —O—, and $A_3$ represents a radical of the formula Ib or Ic, in which $R^{15}$ represents an alkyl radical having from 7 to 30 carbon atoms that is unsubstituted or substituted by hydroxy, amino and/or alkanoylamino having up to 30 carbon atoms, $R^{16}$ represents hydrogen and $R^{17}$ represents 2-hydroxyethyl or 1,2-dihydroxyethyl, the hydroxy groups in a radical $R^{17}$ being etherified by an alkyl radical having from 7 to 30 carbon atoms that is unsubstituted or substituted by hydroxy, amino and/or alkanoylamino having up to 30 carbon atoms, or being esterified by an alkanoyl radical having from 7 to 90 carbon atoms that is unsubstituted or substituted by hydroxy, amino and/or alkanoylamino having up to 30 carbon atoms, or each of $R^{16}$ and $R^{17}$, independently of the other, represents hydroxymethyl in which the hydroxy group is etherified by an alkyl radical having from 7 to 30 carbon atoms that is unsubstituted or substituted by hydroxy, amino and/or alkanoylamino having up to 30 carbon atoms, or is esterified by an alkanoyl radical having from 7 to 90 carbon atoms that is unsubstituted or substituted by hydroxy, amino and/or alkanoylamino having up to 30 carbon atoms, $R_a^9$ preferably represents one of the amino groups and $R_a^{11}$ preferably represents hydroxy, with the proviso that the compounds have at least one, and preferably only one, radical $A^1$, $A^2$ or $A^3$, and of pharmaceutically acceptable salts thereof, and to novel pharmaceutical preparations containing these compounds, The invention relates especially to (g) the use of the D-glucopyranose compounds of the formula I mentioned under (a), (b), (c) and (d) in which $X^1$ represents a group of the formula —NH—, $X^2$ represents a group of the formula —O—, $R^4$, $R^5$, $R^8$ and $R^{10}$ represent hydrogen, and $R^1$, $R^2$, $R^3$, $R^6$, $R^7$, $R^9$, $R^{11}$, $R^{12}$ and $R^{13}$ have the meanings given in the foregoing section for the radicals $R_a^1$, $R_a^2$, $R_a^3$, $R_a^6$, $R_a^7$, $R_a^9$, $R_a^{11}$, $R_a^{12}$ and $R_a^{13}$, respectively, and of pharmaceutically acceptable salts thereof.

The invention relates chiefly to h) the use of compounds of the formula I in which $X^1$ represents a group of the formula —N($R^{14}$)—, $R^{14}$ representing hydrogen or $C_{1-4}$-alkyl, $X^2$ represents oxygen, $R^1$ represents hydrogen, lower alkanoyl, or a group of the formula Ia in which n represents 0 or 1, $Z^1$ represents carbonyl, $Y^1$ represents lower alkylene which may be interrupted by iminocarbonyl, $X^3$ represents oxygen and $A^1$ represents a radical of the formula Ib or Ic in which $R^{15}$ represents an alkyl or alkenyl radical having from 7 to 30 carbon atoms that is unsubstituted or substituted by hydroxy, amino and/or alkanoylamino having up to 22 carbon atoms, $R^{16}$ represents hydrogen and $R^{17}$ represents 2-hydroxyethyl or 1,2-dihydroxyethyl, at least one hydroxy group in a radical $R^{17}$ being etherified by an alkyl or alkenyl radical having from 7 to 30 carbon atoms, or being esterified by an alkanoyl or alkenoyl radical having from 7 to 30 carbon atoms, or each of $R^{16}$ and $R^{17}$, independently of the other, represents hydroxymethyl in which the hydroxy group is etherified by an alkyl or alkenyl radical having from 7 to 30 carbon atoms, or is esterified by an alkanoyl or alkenoyl radical having from 7 to 30 carbon atoms, $R^2$ represents lower alkanoyl, hydroxy-lower alkanoyl, benzoyl or, independently of $R^1$, $R^{12}$ and $R^{13}$, a group of the formula Ia as defined hereinbefore, each of $R^3$, $R^4$, $R^5$, $R^7$ and $R^8$, independently of one another, represents hydrogen, methyl or ethyl, $R^6$ represents hydrogen, or lower alkyl that is unsubstituted or substituted by free hydroxy, free mercapto, lower alkoxy, lower alkylthio, alkanoyloxy having from 2 to 30 carbon atoms, alkenoyloxy having from 6 to 30 carbon atoms, phenyl, 4-hydroxyphenyl, or by a group of the formula Id in which m represents 0 or 1, E represents oxygen or sulphur, $Z^2$ represents carbonyl, $Y^2$ represents lower alkylene that is unsubstituted or substituted by phenyl and may be interrupted by iminocarbonyl, $X^4$ represents oxygen and $A^2$, independently of $A^1$ and $A^3$, represents a radical of the formula Ib or Ic as defined hereinbefore in this Specification, each of $R^9$ and $R^{11}$, independently of the other, represents hydroxy, lower alkoxy, amino, lower alkylamino, carboxy-lower alkylamino, lower alkoxycarbonyl-lower alkylamino, carbamoyl-lower alkylamino, or a radical of the formula Ie in which $X^5$ represents oxygen or NH, $Y^3$ represents lower alkylene which may be interrupted by iminocarbonyl, $X^6$ represents oxygen and $A^3$, independently of $A^1$ and $A^2$, represents a radical of the formula Ib or Ic as defined hereinbefore in this Specification, $R^{10}$ represents hydrogen, $R^{12}$ represents hydrogen, lower alkanoyl or the same radical as $R^{13}$, and $R^{13}$ represents hydrogen, or alkanoyl or alkenoyl each having up to 30 carbon atoms or, independently of $R^1$ and $R^2$, a radical of the formula Ia as defined hereinbefore in this Specification, with the proviso that the compounds contain at least one, and at most two, radicals selected from the group $A^1$, $A^2$ and $A^3$, and the use of pharmaceutically acceptable salts of these compounds.

The invention relates especially to i) the use of compounds of the formula I in which $X^1$ represents the group NH, $X^2$ represents oxygen, $R^1$ represents hydrogen or lower alkanoyl, $R^2$ represents lower alkanoyl, benzoyl or a group of the formula Ia in which n represents 0 or 1, $Z^1$ represents carbonyl, $Y^1$ represents lower alkylene which may be interrupted by one or two iminocarbonyl groups, $X^3$ represents oxygen, and $A^1$ represents a radical of the formula Ib or Ic in which $R^{15}$ represents an alkyl radical having from 7 to 22 carbon atoms, $R^{16}$ represents hydrogen, and $R^{17}$ represents 1,2-dihydroxyethyl in which each of the hydroxy groups, independently of the other, is esterified by an alkanoyl or alkenoyl radical having from 10 to 22 carbon atoms, $R^3$ represents hydrogen or methyl, $R^4$, $R^5$, $R^7$ and $R^8$ each represents hydrogen, $R^6$ represents hydrogen, or lower alkyl that is unsubstituted or substituted by free hydroxy, alkanoyloxy having from 2 to 22 carbon atoms, alkenoyloxy having from 6 to 22 carbon atoms, phenyl or by a group of the formula Id in which m represents 0 or 1, E represents oxygen, $Z^2$ represents carbonyl, $Y^2$ represents lower alkylene that is unsubstituted or substituted by phenyl and may be interrupted by iminocarbonyl, $X^4$ represents oxygen and $A^2$, independently of $A^1$ and $A^3$, represents a radical of the above-defined formula Ib or Ic, each of $R^9$ and $R^{11}$, independently of the other, represents hydroxy, lower alkoxy, amino, lower alkylamino, α-carboxy-lower alkylamino, α-lower alkoxycarbonyl-lower alkylamino, α-carbamoyl-lower alkylamino, or a radical of the formula Ie in which $X^5$ represents the group NH, $Y^3$ represents lower alkylene which may be interrupted by one or two iminocarbonyl groups, $X^6$ represents oxygen and $A^3$, independently of $A^1$ and $A^2$, represents a radical of the formula Ib or Ic defined hereinbefore, $R^{10}$ represents hydrogen, $R^{12}$ represents hydrogen, lower alkanoyl or the same radical as $R^{13}$, and $R^{13}$ represents hydrogen, alkanoyl having from 2 to 22 carbon atoms, alkenoyl having from 6 to 22 carbon atoms or, independently of $R^2$, a radical of the formula Ia as defined hereinbefore, and the use of pharmaceutically acceptable salts of these compounds.

The invention relates most especially to j) the use of compounds of the formula I in which $X^1$ represents the group NH, $X^2$ represents oxygen, $R^1$ represents hydrogen or $C_{2-4}$-alkanoyl, $R^2$ represents $C_{2-4}$-alkanoyl or a group of the formula Ia in which n represents 0 or 1, $Z^1$ represents carbonyl, $Y^1$ represents lower alkylene which may be interrupted by one or two iminocarbonyl groups, $X^3$ represents oxygen, and $A^1$ represents a radical of the formula Ib or Ic in which $R^{15}$ represents an unbranched alkyl radical having from 12 to 18 carbon atoms, $R^{16}$ represents hydrogen and $R^{17}$ represents 1,2-dipalmitoyloxyethyl or 2-oleoyloxy-1-palmitoyloxyethyl, $R^3$ represents hydrogen or methyl, $R^4$, $R^5$, $R^7$, $R^8$ and $R^{10}$ each represents hydrogen, $R^6$ represents methyl, ethyl or isopropyl, each of which is unsubstituted or substituted by a radical of the formula Id in which m represents 0 or 1, E represents oxygen, $Z^2$ represents carbonyl, $Y^2$ represents lower alkylene that is unsubstituted or substituted by phenyl and may be interrupted by one or two iminocarbonyl groups, $X^4$ represents oxygen and $A^2$, independently of $A^1$ and $A^3$, represents a radical of the formula Ib or Ic defined hereinbefore, $R^9$ represents amino, $R^{11}$ represents hydroxy or a radical of the formula Ie in which $X^5$ represents the group NH, $Y^3$ represents lower alkylene which may be interrupted by one or two iminocarbonyl groups, $X^6$ represents oxygen and $A^3$, independently of $A^1$ and $A^2$, represents a radical of the formula Ib or Ic defined hereinbefore, $R^{12}$ represents hydrogen, acetyl or the same radical as $R^{13}$, and $R^{13}$ represents hydrogen, acetyl or, independently of $R^2$, a radical of the formula Ia as defined hereinbefore, and the use of pharmaceutically acceptable salts of these compounds.

The invention relates principally to k) the use of the above-mentioned compounds of the formula I in which the radicals $A^1$, $A^2$ and $A^3$ represent a radical of the formula Ic, and the use of pharmaceutically acceptable salts thereof.

The invention relates especially to l) the use of the above-mentioned compounds of the formula I that carry only one phorphoryl substituent, that is in the radical $R^{11}$ or $R^9$, and the use of pharmaceutically acceptable salts thereof.

The invention relates most especially to m) the use of the compounds of the formula I mentioned above under i) or k) that contain as the sugar moiety a derivative of D-glucose and that, in the case of asymmetric substitution, have at the $C-R^3$ the (D)-configuration, at the $C-R^6$ the (L)-configuration, and at the $C-N-R^8$ the (D)-configuration, and that carry (only) one phorphoryl substituent, that is in the radical $R^9$ or $R^{11}$, wherein, in this phorphoryl substituent of the formula Ie, the radical $A^3$ represents a radical of the formula Ic, which is defined according to h) or j), and the use of pharmaceutically acceptable salts thereof.

The invention relates preferably to the use of compounds of the formula I that have at an asymmetrically substituted $C(-R^3)$-atom the (D)-configuration, at an asymmetrically substituted $C(-R^6)$-atom the (L)-configuration, and at the $C(-N-R^8)$-atom the (D)-configuration, and in which the sugar moiety is derived from (D)-glucose, $X^1$ represents the group NH, $X^2$ represents oxygen, $R^1$, $R^4$, $R^5$, $R^7$, $R^8$, $R^{10}$, $R^{12}$ and $R^{13}$ each represents hydrogen, $R^2$ represents $C_{1-3}$-alkyl or phenyl, $R^3$ represents hydrogen or $C_{1-3}$-alkyl, $R^6$ represents hydrogen, $C_{1-3}$-alkyl optionally substituted by hydroxy, methoxy, mercapto, methylmercapto or by halogen, phenyl or phenylmethyl each optionally substituted by hydroxy, methoxy or halogen, or heterocyclyl or heterocyclylmethyl each containing one or two aza atoms and having 5 ring members, or $R^5$ and $R^6$ together represent trimethylene, one of the radicals $R^9$ and $R^{11}$ represents a radical of the formula Ie in which $X^5$ represents the group NH or oxygen, $Y^3$ represents $C_{2-3}$-alkylene or a radical of the formula

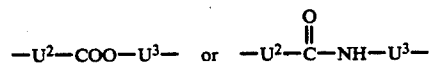

in which each of $U^2$ and $U^3$, independently of the other, represents $C_{1-3}$-alkylene that is unsubstituted or substituted by $C_{1-3}$-alkyl optionally substituted by hydroxy, lower alkoxy, mercapto or by lower alkylmercapto, or by phenyl or phenyl-lower alkyl each of which is optionally substituted by hydroxy, methoxy or halogen, or by heterocyclyl or heterocyclyl-($C_{1-3}$-alkyl) each containing one or two aza atoms and having 5 or 6 ring members, $X^6$ represents oxygen, and $A^3$ represents a radical of the formula Ic in which $R^{16}$ represents hydrogen and $R^{17}$ represents a 1,2-dihydroxyethyl or 2-hydroxyethyl group in each of which at least one of the hydroxy groups is esterified by an aliphatic $C_{16-20}$-carboxylic acid that is optionally singly or doubly unsaturated, or is etherified by an aliphatic $C_{12-18}$-alcohol that is optionally singly or doubly unsaturated, and the other of the radicals $R^9$ and $R^{11}$ represents hydroxy, lower alkoxy, amino, lower alkylamino or aminocarbonyl-lower alkylamino, and the use of pharmaceutically acceptable salts of such compounds.

The invention relates most preferably to the use of compounds of the formula I that have at an asymmetrically substituted $C(-R^3)$-atom the (D)-configuration, at an asymmetrically substituted C(-R⁶)-atom the (L)-configuration and at the C(-N-R⁸)-atom the (D)-configuration, and in which the sugar moiety is derived from (D)-glucose, $X^1$ represents the group NH, $X^2$ represents oxygen, $R^1$, $R^4$, $R^7$, $R^8$, $R^{10}$, $R^{12}$ and $R^{13}$ each represents hydrogen, $R^2$ represents lower alkyl or phenyl, each of $R^3$ and $R^5$, independently of the other, represents hydrogen or methyl, $R^6$ represents $C_{1-4}$-alkyl, $R^9$ represents amino and $R^{11}$ represents a radical of the formula

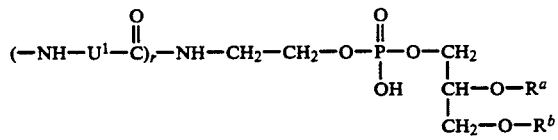

in which r represents 0 or 1, $U^1$ represents a radical of the formula

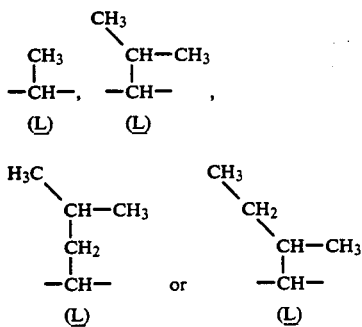

and each of $R^a$ and $R^b$, independently of the other, represents the acyl radical of an alkanoic carboxylic acid having from 12 to 22 carbon atoms or of an unsubstituted aliphatic carboxylic acid having from 12 to 22 carbon atoms and containing one or two double bonds, and the use of pharmaceutically acceptable salts of such compounds.

The invention relates above all to the use in accordance with the invention of the following compounds: the sodium salt of N-acetylmuramyl-L-alanyl-D-isoglutamine-2-(1,2-dipalmitoyl-sn-glycero-4-hydroxyphosphoryloxy)-ethylamide, the sodium salt of N-acetyl desmethylmuramyl-L-alanyl-D-isoglutamine-2-(1,2-dipalmitoyl-sn-glycero-3-hydroxyphosphoryloxy)-ethylamide, the sodium salt of N-acetyldesmethylmuramyl-L-alanyl-D-isoglutamine-2-(1-palmitoyl-2-oleoyl-sn-glycero-3-hydroxyphosphoryloxy)-ethylamide, the sodium salt of N-acetyldesmethylmuramyl-L-alanyl-D-isoglutaminyl-L-alanine-2-(1,2-dipalmitoyl-sn-glycero-3-hydroxyphosphoryloxy)-ethylamide, N-acetylmuramyl-L-alanyl-D-isoglutaminyl-L-alanine-2-(3-palmitoyl-rac-glycero-1-hydroxyphosphoryloxy)-ethylamide, the sodium salt of N-acetylmuramyl-L-α-aminobutyryl-D-isoglutaminyl-L-alanine-2-(1,2-dipalmitoyl-sn-glycero-3-hydroxyphosphoryloxy) -ethylamide, the sodium salt of N-benzoylmuramyl-L-alanyl-D-isoglutaminyl-L-alanine-2-(1,2-dipalmitoyl-sn-glycero-3-hydroxyphosphoryloxy)-ethylamide, N-acetylmuramyl-L-alanyl-D-isoglutaminyl-L-alanine-2-(tetradecyloxyhydroxyphosphoryloxy)-ethylamide, N-acetylmuramyl-L-alanyl-D-isoglutaminyl-L-alanine-2-(hexadecyloxyhydroxyphosphoryloxy)-ethylamide, the sodium salt of N-acetylmuramyl-L-α-aminobutyryl-D-isoglutaminyl-L-alanine-2-[(3R)-hydroxy-(2S)-palmitoylamino-4t-octadecenyloxyhydroxyphosphoryloxy]-ethylamide, the sodium salt of N-acetylmuramyl-L-α-aminobutyryl-D-isoglutaminyl-L-alanine-2-[(3R)-α-hydroxy-(2S)-palmitoylaminooctadecyloxyhydroxyphosphoryloxy]-ethylamide, the sodium salt of N-acetylmuramyl-L-alanyl-D-isoglutaminyl-L-alanine-2-(cholest-5-en-3β-oxyhydroxyphosphoryloxy]-ethylamide, the sodium salt of N-acetylmuramyl-L-O-{(N-[2-(1-palmitoyl-2-oleoyl-sn-glycero-3-hydroxyphosphoryloxy)-ethyl] -succinamoyl)-glycyl}-seryl-D-isoglutamine, the sodium salt of N-acetylnormuramyl-L-O-(1,2-dipalmitoyl-rac-glycero-3-hydroxyphosphoryl)-seryl-D-isoglutamine, the sodium salt of N-acetyl-6-O-([1,2-dipalmitoyl-rac-glycero-3-hydroxyphosphoryloxy]-acetyl)-normuramyl-L-alanyl-D-isoglutamine, the sodium salt of N-acetyl-6-O-(1,2-dipalmitoyl-rac-glycero-3-hydroxyphosphoryloxy)-normuramyl-L-alanyl-D-isoglutamine, the sodium salt of N-{N-[2-(1,2-dipalmitoyl-sn-glycero)-3-hydroxyphosphoryloxy]-ethyl}-succinamoylmuramyl-L-alanyl-D-isoglutamine, the sodium salt of N-acetyl-6-O-{N-[2-(1,2-dipalmitoyl-sn-glycero-3-hydroxyphosphoryloxy)-ethyl]-succinamoyl}-muramyl-L-α-aminobutyryl-D-isoglutamine, the sodium salt of N-acetylnormuramyl-L-O-{N-[2-tetradecyloxyhydroxyphosphoryloxy)-ethyl]-succinamoyl}-seryl-D-isoglutamine, the sodium salt of N-acetylmuramyl-L-O-{[N-(1-palmitoyl-2-oleoyl-sn-glycero-3-hydroxyphosphoryloxy)-ethyl]-succinamoyl-L-phenylalanyl}-seryl-D-isoglutamine, the sodium salt of N-acetylmuramyl-L-O-(hexadecyloxyhydroxyphosphoryl)-seryl-D-isoglutamine and the sodium salt of N-acetylmuramyl-L-O-(1,2-dipalmitoyl-3-sn-glycerohydroxyphosphoryl)-seryl-D-isoglutamine.

The invention relates especially to the use of the compounds of the formula I described in the Examples, and of the pharmaceutically acceptable salts thereof, and above all to the use of N-acetylmuramyl-L-alanyl-D-isoglutaminyl-L-alanine-2-(1,2-dipalmitoyl-sn-glycero-3-hydroxyphosphoryloxy)-ethylamide, especially the sodium salt of this compound, referred to hereinafter as compound I.

BRIEF DESCRIPTION OF DRAWINGS

FIG. 7, Part II (FIG. 7c and FIG. 7d) shows effect of intranasally administered compound I on mice infected with Parainfluenza Virus I (Sendai)/56. Statistical significance *P≦0,05, **P≦0,01 (Vierfelder test).

Figure 1:
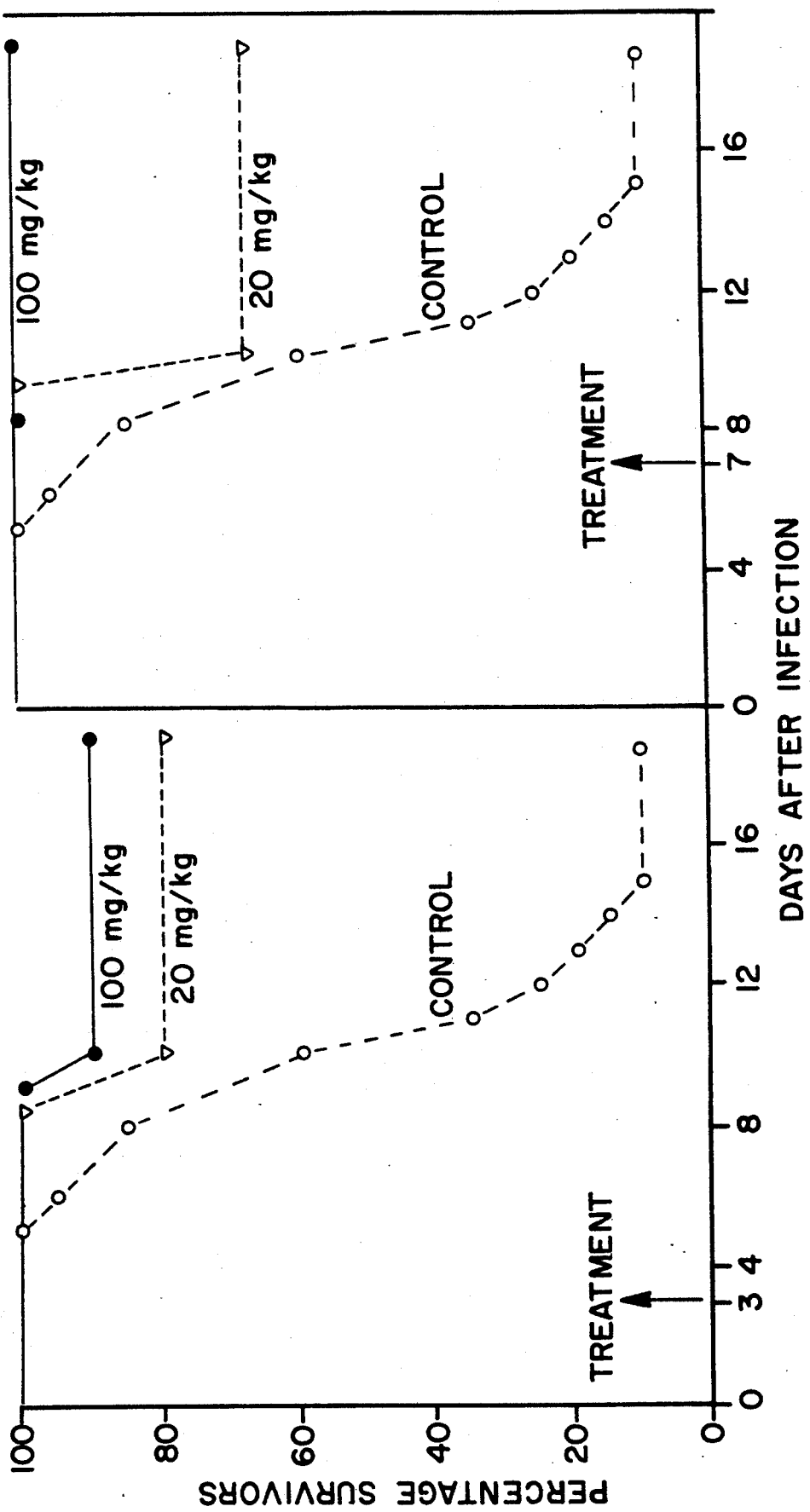
FIG. 1 shows therapeutic effect of orally administered compound I (single dose on day 3) on a group of 10 mice infected intranasally with the virus strain Influenza A/Victoria/3/75 (20 mice in the control group).

The following Examples illustrate the invention but do not limit the invention in any way.

EXAMPLE 1

Groups of 30, 40 or 50 female MF-2f SPF mice each having a body weight of 14–16 g, or of 12–14 g in the case of tests with herpes simplex 1 viruses, are infected intranasally, under light anaesthesia using a mixture of equal parts of ether, ethanol and chloroform, with lethal doses (approximately $LD_{80-90}$; number of plaque-forming units [PFU] see Table 1) of the undermentioned virus strains in the form of 0.05 ml in each case of a suspension of the viruses.

At the time indicated below (days) in relation to the day of infection, 10 or 20 of these mice are administered once (single dose) the quantities indicated in Table 1 of the active ingredient, the sodium salt of N-acetylmuramyl-L-alanyl-D-isoglutaminyl-L-alanine-2-(1,2-dipalmitoyl-sn-glycero-3-hydroxyphosphoryloxy)-ethylamide (compound I), in 0.05 ml or 0.1 ml of phosphate-buffered salt solution (PBS) or in 0.2 ml of a 0.05% by weight solution of sodium carboxymethylcellulose in double-distilled water, by means of intranasal, intravenous or oral administration respectively, in the manner indicated in Table 1.

The remainder of the above-mentioned mice, that is 20 or 30, serve as the control, that is to say they either receive no treatment or are given a placebo.

The intranasal administration of compound I is effected under light anaesthesia using a mixture of equal parts of diethyl ether, ethanol and chloroform.

TABLE 1

| Virus [PFU] | Mode of administration | Time of administration [days] −: before infection +: after infection | Percentage of mice surviving 20 days after infection in dependence on the quantity of active ingredient [mg/kg] statistical significance $^xP \leq 0.05$, $^{xx}P \leq 0.01$ (Vierfelder test) | | | | | | | |
|---|---|---|---|---|---|---|---|---|---|---|
| | | | 500 | 100 | 20 | 10 | 1 | 0.1 | 0 | control |
| Influenza A/ Victoria/3/75 (H3N2) (mouse-adapted) [2 × 10³ − 1 × 10⁴ PFU] | intravenous | −7 | | 80$^{xx}$ | | 90$^{xx}$ | 30 | | | 20 |
| | | −5 | | 80$^{xx}$ | | 80$^{xx}$ | 30 | | | |
| | | −1 | | 80$^{xx}$ | | 80$^{xx}$ | 70$^x$ | | | |
| | | 0 | | 90$^{xx}$ | | 100$^{xx}$ | 70$^x$ | | | |
| | | +1 | | 90$^{xx}$ | | 70$^x$ | 60 | | | |
| | intranasal | −14 | | | | 60 | 70$^{(x)}$ | 80$^x$ | | 40 |
| | | −7 | | | | 100$^{xx}$ | 100$^{xx}$ | 80$^x$ | | |
| | oral | +3 | 70$^{xx}$ | 90$^{xx}$ | 80$^{xx}$ | | | | | 15 |
| | | +7 | 100$^{xx}$ | 100$^{xx}$ | 70$^{xx}$ | | | | | |
| Influenza A/ USSR/92/77 (H1N1) (mouse-adapted) [3 × 10² − 1 × 10³ PFU] | intravenous | −7 | | 66$^x$ | | 40 | 40 | | | 10 |
| | | −2 | | 60$^x$ | | 70$^{xx}$ | 50$^x$ | | | |
| | | −1 | | 70$^x$ | | 70$^{xx}$ | 50$^x$ | | | |
| | | 0 | | 100$^{xx}$ | | 80$^{xx}$ | 60$^x$ | | | |
| | | +1 | | 90$^{xx}$ | | 90$^{xx}$ | 60$^x$ | | | |
| | | +2 | | 90$^{xx}$ | | 50$^{xx}$ | 40 | | | |
| | | +6 | | 60$^x$ | | 60$^x$ | 40 | | | |
| Influenza A/ Texas/1/77 (H3N2) (mouse-adapted) [2 × 10⁰ − 1 × 10¹ PFU] | intranasal | −7 | | | | 50$^{xx}$ | 40$^x$ | 30$^{(x)}$ | | 0 |
| | | −7 | | | | 100$^{xx}$ | 90$^x$ | 70$^{(x)}$ | | 35 |
| | oral | +7 | | | | 65$^{xx}$ | | | | 0 |

| Virus [PFU] | Mode of administration | Application time | Percentage survivors | | | | | | |
|---|---|---|---|---|---|---|---|---|---|
| | | | 500 | 100 | 20 | 10 | 1 | 0.1 | 0 |
| Influenza B/ Hong Kong/5/72 [3 × 10⁵ − 1 × 10⁶ PFU] | intravenous | −7 | | 90$^x$ | | 70 | 70 | | 42 |
| | | −5 | | 90$^x$ | | 100$^{xx}$ | 80$^{(x)}$ | | |
| | | −2 | | 100$^{xx}$ | | 90$^x$ | 100$^{xx}$ | | |
| | | −1 | | 100$^{xx}$ | | 90$^x$ | 80$^{(x)}$ | | |
| | | 0 | | 100$^{xx}$ | | 100$^{xx}$ | 90$^x$ | | |
| | | +1 | | 80$^{(x)}$ | | 80$^{(x)}$ | 60 | | |
| | | +2 | | 100$^{xx}$ | | 70 | 90$^x$ | | |
| | | +6 | | 100$^{xx}$ | | 80$^{(x)}$ | 70 | | |
| | intranasal | −7 | | | | 100$^{xx}$ | 80$^x$ | 80$^x$ | 30 |
| | oral | +3 | | 50$^x$ | | | 50$^x$ | | 15 |
| | | +7 | | 80$^{xx}$ | | 90$^{xx}$ | 50$^x$ | | |
| Influenza B/ Ann Arbor (Ms.Lu.25.Russ) (mouse-adapted) [1 × 10¹ PFU] | intranasal | −14 | | | | 50$^x$ | 20 | 20 | 0 |
| | | −7 | | | | 80$^{xx}$ | 50$^x$ | 20 | |
| | oral | +3 | | 100$^{xx}$ | | 90$^{xx}$ | 80$^{xx}$ | | 15 |
| | | +7 | | 100$^{xx}$ | | 80$^{xx}$ | 80$^{xx}$ | | |
| Encephalomyocarditis [1 × 10¹ − 1 × 10² PFU] | oral | 0 | | 80$^x$ | | 100$^{xx}$ | 60 | | 30 |
| | | +2 | | 60 | | 80$^x$ | 90$^{xx}$ | | |
| | | +4 | | 100$^{xx}$ | | 70$^{(x)}$ | 90$^{xx}$ | | |
| Herpes Simplex 1/TUP | intranasal | −7 | | | | 70$^x$ | 60$^x$ | 60$^x$ | 20 |

TABLE 1-continued

| | | | | | | | |
|---|---|---|---|---|---|---|---|
| [2 × 10⁴ PFU] Herpes Simplex 1/Virtue [2 × 10³ PFU] | intranasal | −7 | | 90$^x$ | 100$^x$ | 70 | 40 |

Figure 2:
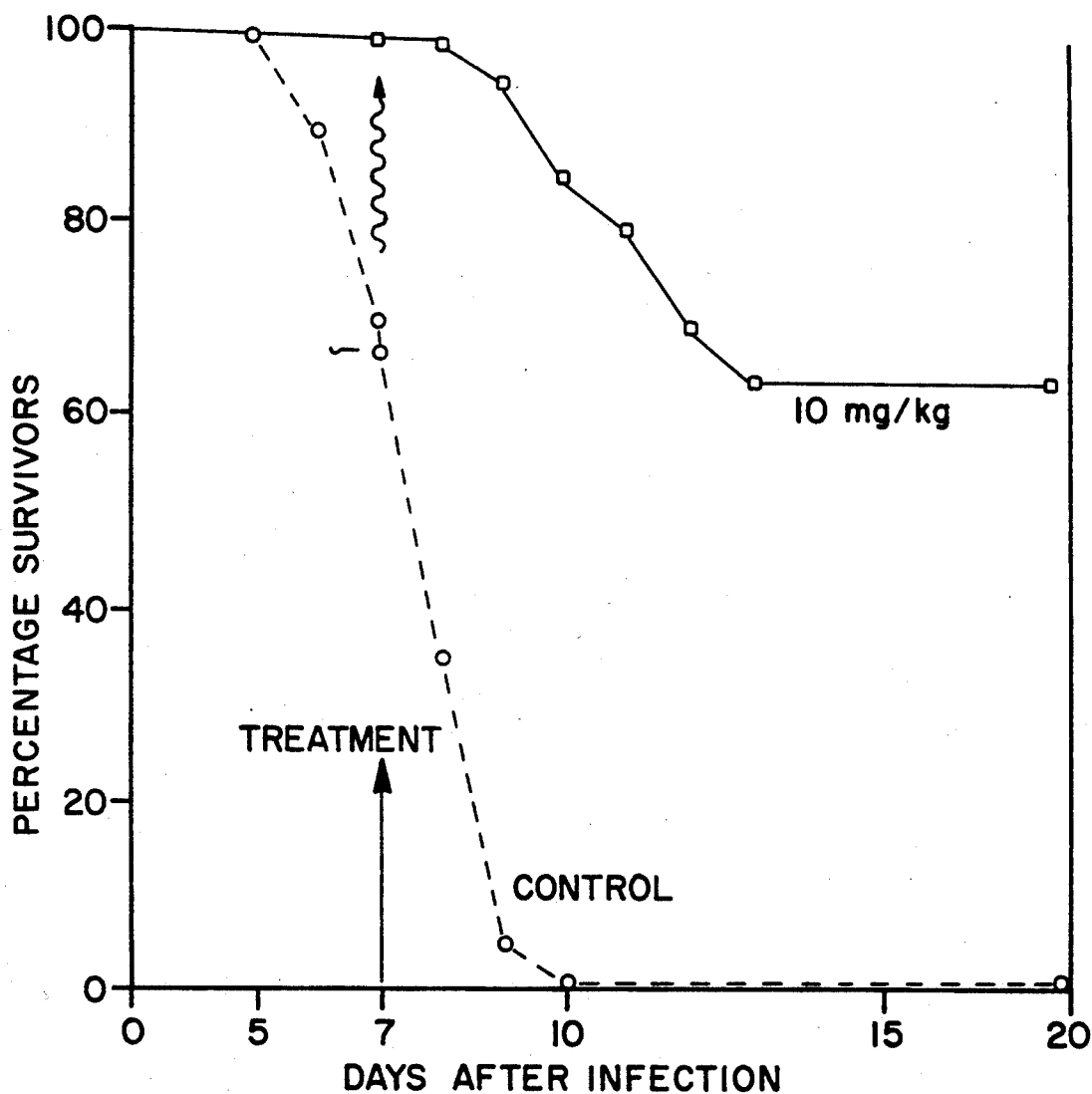
FIG. 2 shows therapeutic effect of orally administered compound I (single dose on day 7) on a group of 30 mice infected intranasally with the virus strain Influenza A/Texas/1/77 (20 mice in the control group).

The course of some of the above-described infections over a period of time is illustrated in FIGS. 1 and 2.

The great superiority of the phosphoryl compounds of the formula I over muramyl peptides, such as N-acetylmuramyl-L-alanyl-D-glutamine-n-butyl ester (compound II) is demonstrated, for example, by the fact that in the case of the above-mentioned tests carried out for comparison purposes, on oral administration of 10 mg of the latter compound on day +7 all the mice die from infection with Influenza A/Texas/1/77, whilst on administration of the same quantity of the phosphoryl-muramyl peptide compound I at the same time, as can be seen in the Table, 65% of the mice survive the infection.

Furthermore, on intranasal administration of 1 mg/kg of compound II on day −7 it is not possible to detect any kind of protective action in the case of infection with Influenza A/Texas/1/77, whilst on administration of the same quantity of compound I at the same time 90% of the mice survive the infection.

Figure 3:
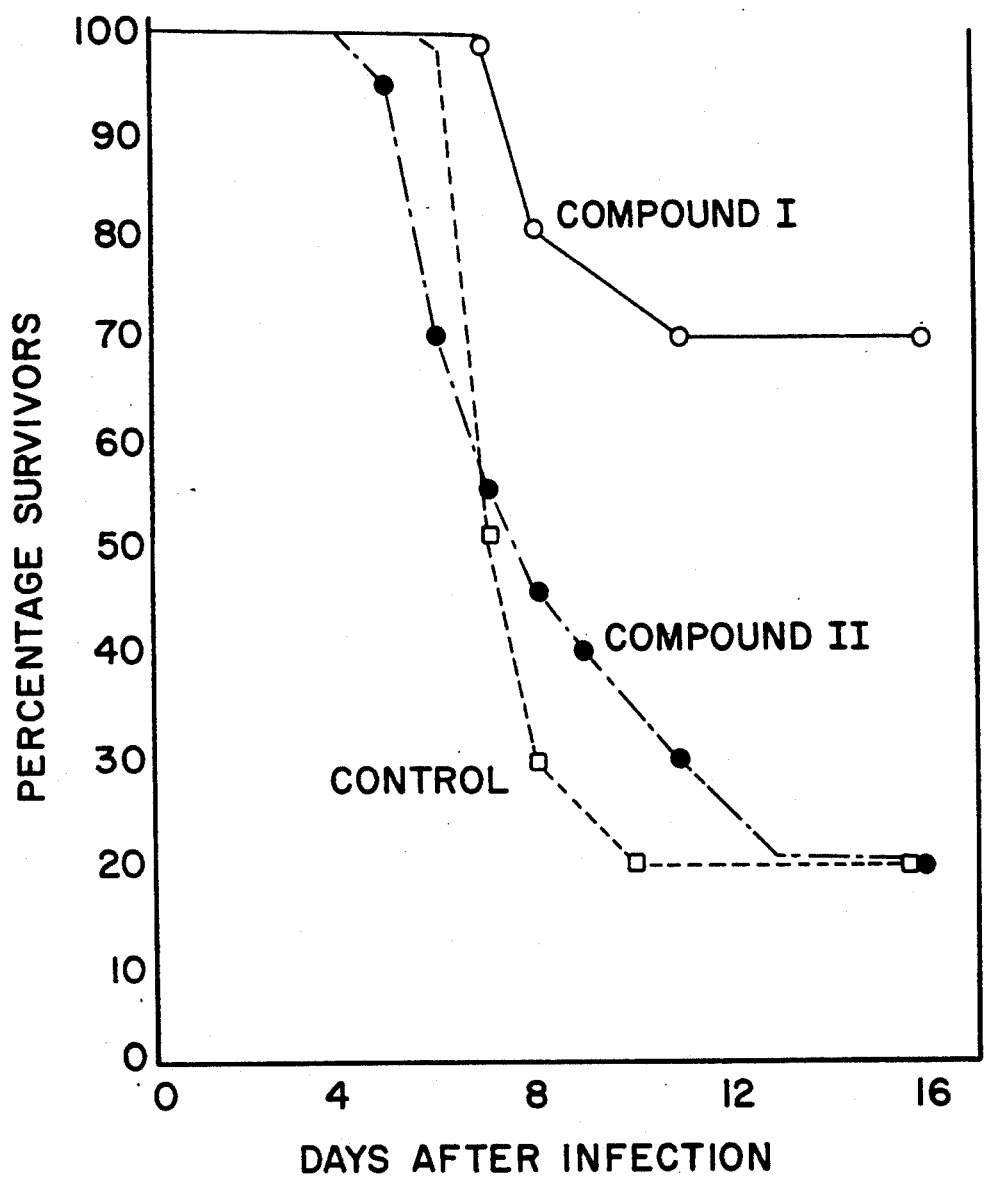
FIG. 3 shows prophylactic effect of, in each case, 10 mg/kg (single dose on 7th day before infection) of intranasally administered compound I or compound II on a group of 10 mice infected intranasally with the Herpesvirus hominis 1/TUP (20 mice in the control group).

It is also not possible to detect any kind of protective action on intranasal administration of 10 mg/kg of compound II on day −7 in the case of intranasal infection with *Herpesvirus hominis* 1/TUP, as can be seen from FIG. 3.

EXAMPLE 2

The number indicated in the following Table of female albino guinea pigs of the Pirbright strain (150–180 g body weight) are infected intravaginally with ~10⁴ PFU (plaque-forming units) of *Herpesvirus hominis* 2/Angelotti, cultivated in HEL (human embryonal lungs) cells, as described in B. Lukas et al., Arch. ges. Virusforsch. 44, 153-155 (1974).

At the time indicated in the following Table (the time difference in days in relation to the day of infection, − [minus] indicating a time before infection) the number N of guinea pigs indicated in Table 2 are treated intravaginally with a single dose of in each case 0.1 ml of a gel containing the concentration of compound I indicated in Table 2.

The gel without active ingredient has the following composition:

| |
|---|
| 2.25% sodium carboxymethylcellulose (Hercules, USA) |
| 10% glycerine |
| made up to 100% with bi-distilled water. |

The effect of the treatment can be seen in Table 2.

The symptoms occurring in untreated animals are described in B. Lukas et al., Arch. Virol. 49, 1-11 (1975).

TABLE 2

Effect on local symptoms in the topical chemotherapy of Herpes genitalis in guinea pigs
(statistical significance $^xP < 0.05$, $^{xx}P < 0.01$ in the Fisher test)

| Active ingredient concentration [%] | Treatment time [days] | N | Animals [%] with regression of symptoms of ≧ 66% on day | | | | Symptom-free animals [%] on day | | | |
|---|---|---|---|---|---|---|---|---|---|---|
| | | | 7 | 10 | 12 | 14 | 10 | 12 | 14 | 21 | 34 |
| 1.0 | −7 | 14 | 29 | 79$^{xx}$ | 71$^{xx}$ | 93$^{xx}$ | 21 | 57$^x$ | 86$^{xx}$ | 86$^x$ | 100$^x$ |
| 0.1 | −7 | 14 | 21 | 57$^x$ | 86$^{xx}$ | 100$^{xx}$ | 43$^x$ | 64$^{xx}$ | 86$^{xx}$ | 86$^{xx}$ | 100$^{xx}$ |
| 1.0 | +4 | 14 | 79$^{xx}$ | 79$^{xx}$ | 86$^{xx}$ | 93$^{xx}$ | 36 | 64$^{xx}$ | 79$^{xx}$ | 86$^{xx}$ | 100$^{xx}$ |
| 0.1 | +4 | 13 | 62$^{xx}$ | 85$^{xx}$ | 100$^{xx}$ | 93$^{xx}$ | 70$^{xx}$ | 77$^{xx}$ | 85$^{xx}$ | 100$^{xx}$ | 100$^{xx}$ |
| 0 (placebo) | +4 | 14 | 0 | 0 | 0 | 0 | 0 | 0 | 0 | 0 | 0 |
| control (untreated) | | 20 | 0 | 0 | 0 | 0 | 0 | 0 | 0 | 0 | 20 |

EXAMPLE 3

Eye Drops

| Composition: | |
|---|---|
| compound I | 0.10 mg |
| boric acid | 30.00 mg |
| sodium tetraborate.10H$_2$O | 0.10 mg |
| benzalkonium chloride | 0.20 mg |
| water for injection | to make up to 1.00 ml |

Preparation

The boric acid, sodium tetraborate and benzalkonium chloride are dissolved while stirring at room temperature under aseptic conditions in a portion of the above-mentioned quantity of water for injection. CGP 19835 is then dissolved in the resulting solution, and water for injection is added to make up to the final volume of 1.0 ml.

The solution, or a portion or a multiple thereof, is filtered through a membrane filter and introduced into cleaned containers. Suitable containers are, for example: flexible plastics containers (5 ml or 10 ml) having a dropping attachment,
glass containers (5 ml or 10 ml) having a glass or plastics dropping pipette and an elastomeric pipette filler, or plastics single-dose pipettes (contents 1–2 drops).

EXAMPLE 4

Non-Aqueous Single Dose for Nasal Administration

| Composition: | |
|---|---|
| compound I | 0.03 mg |
| Miglyol 812 | to make up to 30.00 mg |

Preparation 0.03 mg of compound I is dissolved under aseptic conditions in 29.97 mg of Miglyol 812.

This solution is introduced into a commercially available single-dose nasal applicator, for example an applicator according to U.S. Pat. No. 3,739,951, which is attached to an aerosol-container before use.

EXAMPLE 5

Nose Drops

| Composition: | I | II |
|---|---|---|
| compound I | 0.15 mg | 0.10 mg |
| thiomersal | 0.02 mg | — |
| sodium monohydrogen phosphate.2H$_2$O | 0.30 mg | 0.30 mg |
| sodium dihydrogen phosphate.12H$_2$O | 10.10 mg | 10.10 mg |
| benzalkonium chloride | — | 0.10 mg |
| disodium salt of ethylenediaminetetra-acetic acid (EDTA) | 0.50 mg | 0.50 mg |
| sodium chloride | 3.70 mg | 4.50 mg |
| demineralised water | 988.30 mg | 987.60 mg |
| pH value: | 5.0 ± 0.3 | 5.0 ± 0.3 |
| lowering of freezing point Δt | −0.51° C. | −0.56° C. |

Preparation

While stirring at room temperature, the sodium dihydrogen phosphate, disodium monohydrogen phosphate, sodium chloride, thiomersal and the disodium salt of EDTA are dissolved in a portion of the above-mentioned quantity of demineralised water.

Compound I is then dissolved in this solution and the whole is supplemented with the remaining demineralised water.

The solution, or a portion or a multiple thereof, is filtered through a membrane filter and introduced into cleaned containers.

Suitable containers are, for example:

a) glass or plastics containers (5 ml or 10 ml) having a glass or plastics pipette with an elastomeric pipette filler b) compressible plastics bottles having a central tube and a plastics spraying head c) single-dose plastics containers (contents 2–3 drops), or d) glass or plastics bottles that are provided with a standardised pumpable dosing spray made of plastics (no propellant).

EXAMPLE 6

Gel

| Composition: | |
|---|---|
| compound I | 0.01 g |
| glycerine 85% | 10.00 g |
| methyl paraben | 0.12 g |
| propyl paraben | 0.03 g |
| sodium carboxymethylcellulose (high viscosity) | 2.50 g |
| demineralised water | 87.34 g |

Preparation

The methyl paraben and propyl paraben are dissolved in a portion of the hot demineralised water. The sodium carboxymethylcellulose is then incorporated into the resulting solution while stirring vigorously. While stirring, the glutinous product is allowed to swell. After cooling, the glycerine and a solution of the active ingredient, compound I, in the remaining water are then added to this product.

EXAMPLE 7

Cream

| Composition: | |
|---|---|
| compound I | 0.10 g |
| sorbitan monostearate | 0.60 g |
| cetyl alcohol | 3.00 g |
| isopropyl palmitate | 2.00 g |
| methyl paraben | 0.12 g |
| paraffin oil, viscous | 10.00 g |
| PEG (20)-sorbitan monostearate | 4.40 g |
| propyl paraben | 0.03 g |
| 70% solution of crystalline sorbitol in demineralised water | 6.00 g |
| stearic acid | 9.00 g |
| demineralised water | 64.67 g |

Preparation

The fatty phase, comprising sorbitan monostearate, cetyl alcohol, stearic acid, PEG (20)-sorbitan monostearate, isopropyl palmitate and paraffin oil, is melted. The methyl paraben and propyl paraben are then dissolved in a portion of the hot demineralised water. The sorbitol solution is added to the aqueous phase. While stirring, the aqueous phase is then added at approximately 75° C. to the fatty phase. The cream base is then allowed to cool while stirring. A solution of the active ingredient, compound I, in the remaining water is then added to the cream base at approximately 40° C.

EXAMPLE 8

Nasal ointment

| Composition: | |
|---|---|
| compound I | 0.03 g |
| paraffin oil, viscous | 20.00 g |
| white petroleum jelly | 30.00 g |
| wool fat, anhydrous | 40.00 g |
| demineralised water | 19.97 g |

Preparation

The fatty phase, comprising paraffin oil, petroleum jelly and wool fat, is melted. The aqueous solution of the active ingredient is incorporated into the fatty phase at approximately 50° C.

EXAMPLE 9

Skin ointment

| Composition | |
|---|---|
| compound I | 0.25 g |
| sorbitan sesquioleate | 10.00 g |
| white beeswax | 5.00 g |
| cetyl alcohol | 2.50 g |
| methyl paraben | 0.15 g |
| paraffin oil, viscous | 20.00 g |
| propyl paraben | 0.02 g |
| stearyl alcohol | 2.50 g |
| white petroleum jelly | 40.00 g |

-continued

| Composition | |
|---|---|
| demineralised water | 19.58 g |

Preparation

The fatty phase, comprising sorbitan sesquioleate, white beeswax, cetyl alcohol, paraffin oil, stearyl alcohol and white petroleum jelly is melted. The methyl paraben and propyl paraben are then dissolved in the main quantity of the water at elevated temperature. The aqueous phase is incorporated into the fatty phase at approximately 80° C. A solution of the active ingredient, compound I, in the remaining water is added to the resulting ointment base at approximately 40° C.

EXAMPLE 10

Lipstick

| Composition: | |
|---|---|
| compound I | 1.00 g |
| polyethylene glycol having an average molecular weight of 400. | 15.00 g |
| polyethylene glycol having an average molcular weight of 1000 | 83.00 g |
| polyethylene glycol having an average molecular weight of 4000 | 1.00 g |

Preparation

The active ingredient is finely dispersed in the molten polyethylene glycols. The viscous melt is poured into suitable lipstick cases and left to harden.

EXAMPLE 11

Preparation of compound I

A solution of 1.5 mmol of N-acetylmuramyl-L-alanyl-D-isoglutaminyl-L-alanine-N-hydroxysuccinimide ester in 5 ml of dimethyl acetamide is added dropwise to a solution of 1 mmol of 2-(1,2-dipalmitoyl-sn-glycero-3-hydroxyphosphoryloxy)-ethylamine and 3.5 mmol of N-ethylmorpholine in 25 ml of chloroform:methanol:-water= 65:25:4. After stirring for 8 hours at room temperature the reaction is complete. 130 ml of water are added to the reaction mixture. Chloroform and portions of the methanol are distilled off under reduced pressure. The aqueous solution is filtered through a millipore filter made of Teflon (pore size 5 μm). The filtrate is dialysed, while stirring, in an Amicon ultrafiltration cell through an Amicon YM 10 membrane (consisting of polysaccharide; nominal molecular weight cut off: 10 000 dalton) in a diafiltration process firstly against water (400 ml), then against 0.1M sodium phosphate buffer-0.1M NaCl, pH 7 (200 ml), and subsequently against water (850 ml). The internal dialysate is filtered through a millipore filter, pore size 0.45 μm, and freeze-dried, yielding the sodium salt of N-acetyl-muramyl-L-alanyl-D-isoglutaminyl-L-alanine-2-(1,2-dipalmitoyl-sn-glycero-3-hydroxyphosphoryloxy)-ethylamide hydrate.

EXAMPLE 12

Groups of 20 female Tif:MF-2f (SPF) mice each having a body weight of 14–16 g are infected intravenously, under light anaesthesia using a mixture of equal parts of diethyl ether, ethanol and chloroform, with $2 \times 10^3$ PFU vaccinal virus IHD in the form of in each case 0.1 ml of a suspension of the virus in beef heart infusion broth.

10 of these mice from each of the above-mentioned groups are treated on the fourth or sixth day after infection, that is to say on day +4 or +6 (administration day), with a single oral administration of 1 mg/kg of compound I in 0.2 ml of a 0.05% by weight aqueous solution of sodium carboxymethylcellulose.

The remaining 10 mice from each of the above-mentioned groups serve as the controls and receive a placebo.

On the seventh, ninth, tenth and twelfth day after infection the number of tail lesions in the mice is determined, this being carried out substantially as described by J. J. Boyle, R. F. Haff and R. C. Stewart in Antimicrobial Agents and Chemotherapy, 536–539 (1967), and it should be noted that the first tail lesions can be identified only on the sixth or seventh day. The results can be seen in Table 3:

TABLE 3

| Day of administration | Number of tail lesions (mean ± standard deviation) on day | | | |
|---|---|---|---|---|
| | +7 | +9 | +10 | +12 |
| +4 | 0.9 ± 0.7* | 0.9 ± 0.9* | 0.9 ± 1.4* | 0.2 ± 0.4* |
| +6 | 1.1 ± 1.4* | 0.9 ± 1.6* | 0.3 ± 0.7* | 0.5 ± 1.0* |
| control | 4.3 ± 1.9 | 4.3 ± 1.9 | 5.9 ± 1.9 | 4.6 ± 1.8 |

*statistical significance $P \leq 0.01$ (Student's T-test)

EXAMPLE 13

Figure 4:
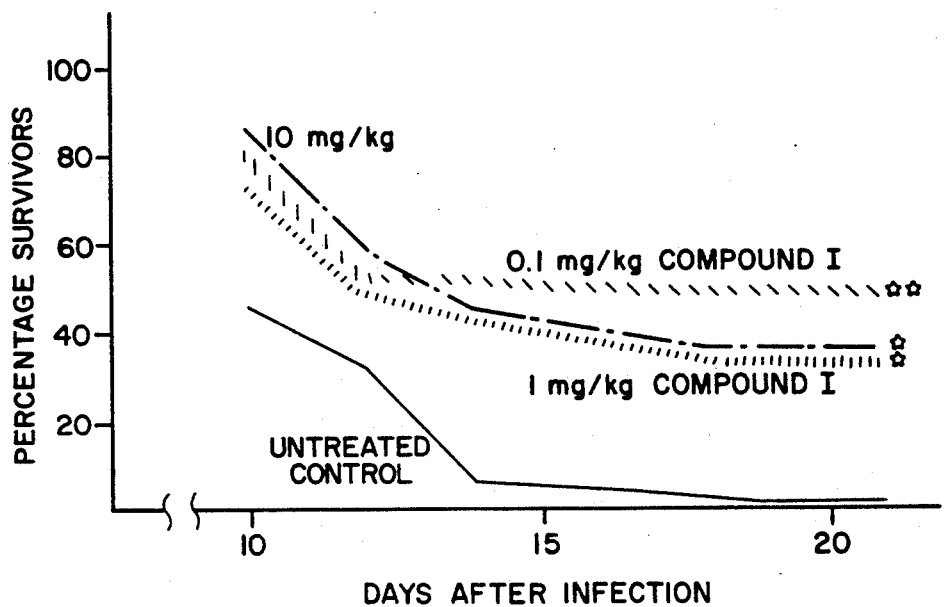
FIG. 4 shows therapeutic effect of orally administered compound I on guinea pigs infected with Herpes simplex Virus 2/Alabama. Statistical significance *P≦0,05, **P≦0,01 (Vierfelder test).

Groups of 50–54 female albino guinea pigs of the Pirbright strain (150–180 g body weight) are infected intravaginally with $1 \times 10^3$ PFU of the neurotropic virus strain Herpes simplex 2/MS in a manner analogous to Example 2. In the case of the Alabama strain, on the third day after infection 15 to 18 of these guinea pigs are administered orally a single dose, as indicated in FIG. 4, of compound I in 0.2 ml of a 0.005% by weight aqueous solution of sodium carboxymethylcellulose. In the case of the MS strain, on the seventh day before infection 17 to 19 of the above-mentioned guinea pigs, under light anaesthesia using a mixture of equal parts of diethyl ether, ethanol and chloroform, are administered intranasally a single dose, as indicated in FIG. 5, of compound I in 0.2 ml of a 0.005% by weight aqueous solution of sodium carboxymethylcellulose.

Figure 5:
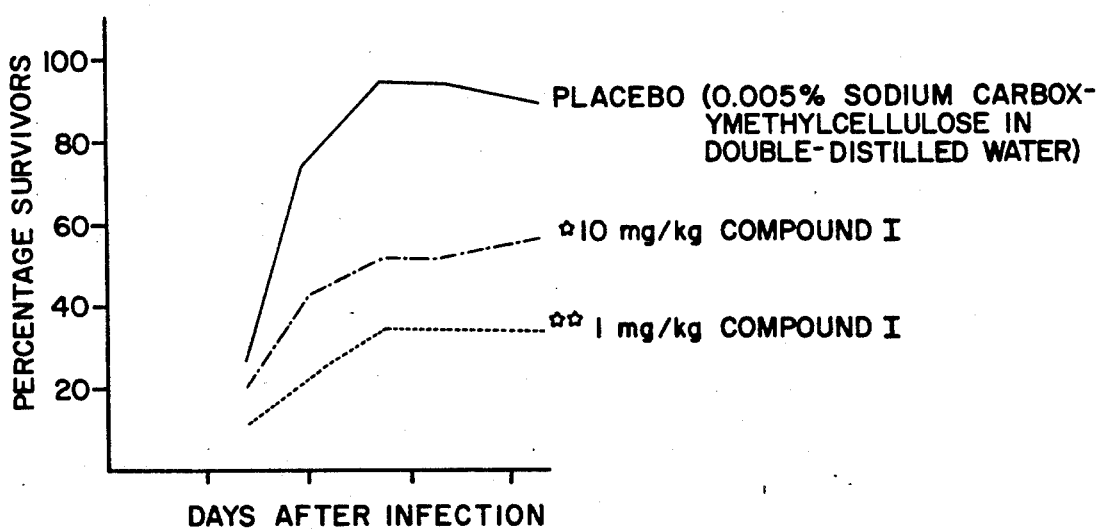
FIG. 5 shows prophylactic effect of intranasally administered compound I on guinea pigs infected with Herpes simplex Virus 2/MS. Statistical significance *P≦0,005, **P≦0,01 (Vierfelder test).

The control groups each comprise 35 animals and receive no treatment (FIG. 4) or are given a placebo (FIG. 5). The results are shown in FIGS. 4 and 5, respectively.

EXAMPLE 14

Groups of 30 or 34 female Tif:MF 2f (SPF) mice each having a body weight of 14–16 g are infected intranasally under light anaesthesia with from 10 to 50 PFU of Parainfluenza Virus 1 (Sendai)/52 (mouse-adapted, stored at −70° C. in the form of a mouse-lung suspension in ampoules). For the above-mentioned anaesthesia there is used a mixture of equal parts of diethyl ether, alcohol and chloroform.

At the time indicated in FIGS. 6 and 7, 10 (in the case of FIG. 6) and 14 (in the case of FIG. 7) of these mice are administered once the quantities indicated in the Figures of compound I in 0.2 ml of 0.005% by weight sodium carboxymethylcellulose in double-distilled water in the manner indicated in the Figures, in the case of intranasal administration of the active ingredient before infection under anaesthesia using a mixture of equal parts of diethyl ether, alcohol and chloroform and in the case of intranasal administration of the active ingredient after infection under anaesthesia using Nembutal (0.5 mg/mouse, intraperitoneal), followed after 20-25 minutes by intranasal administration by drip of 0.02 ml of 1% aqueous cinchocaine hydrochloride solution.

The remaining 20 mice from each of the above-mentioned groups serve as the control. The control animals either receive no treatment or are given a placebo.

Figure 6A:
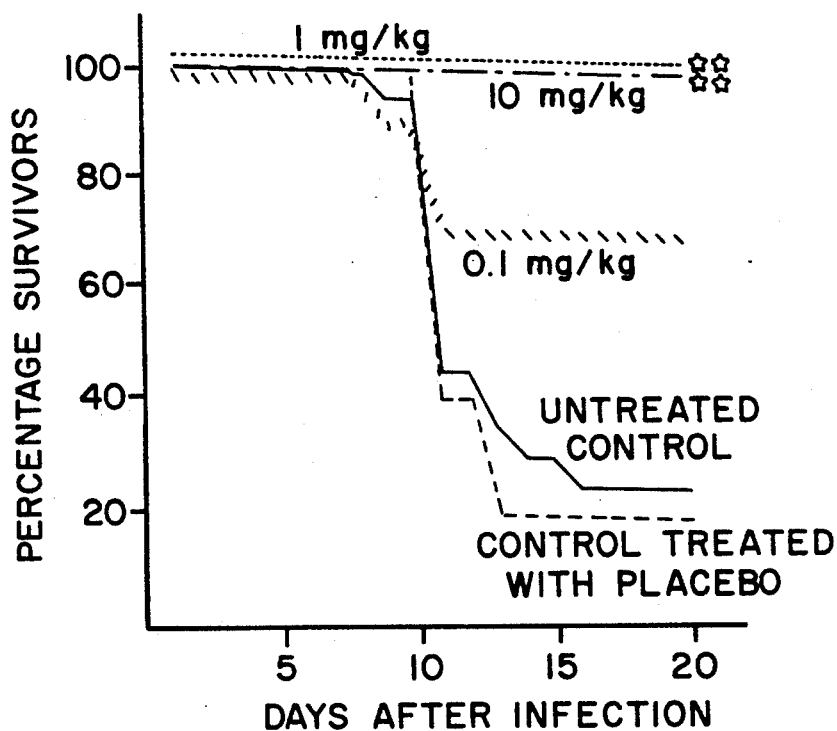
(FIG. 6a shows administration of active ingredient on 3rd day after infection and FIG. 6b shows administration of active ingredient on 7th day after infection).
Figure 6B:
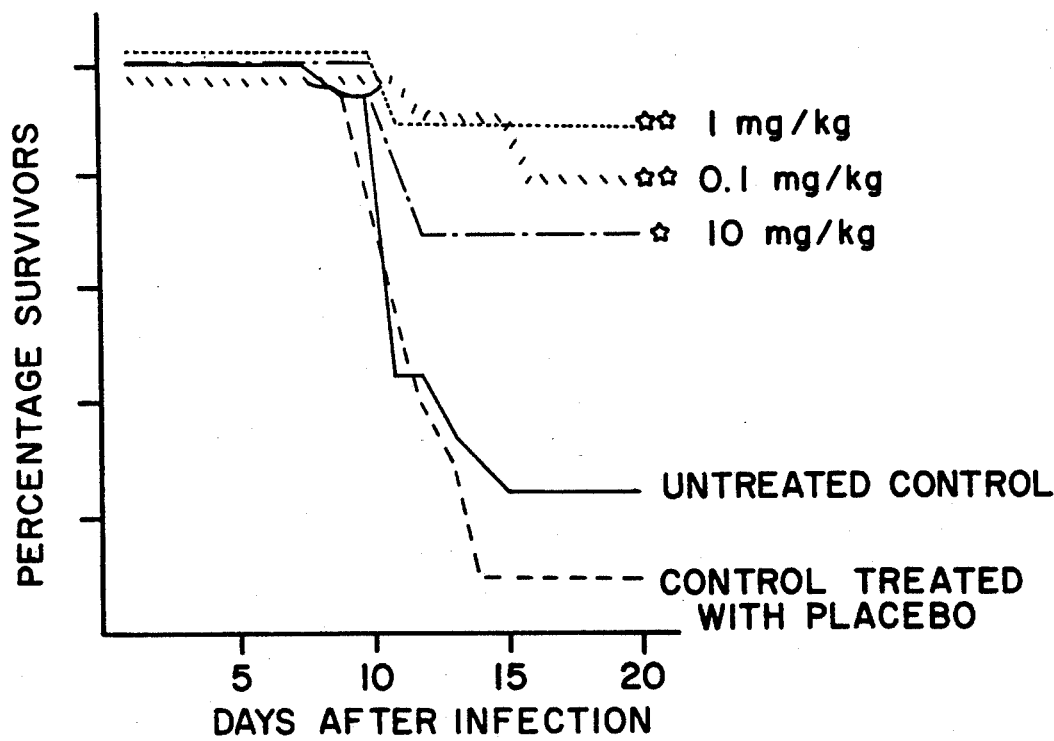
FIG. 6 (FIG. 6a and FIG. 6b) shows therapeutic effect of orally administered compound I on mice infected with Parainfluenza Virus I (Sendai)/52. Statistical significance *P≦0,05, **P≦0,01 (Vierfelder test).
Figure 7A:
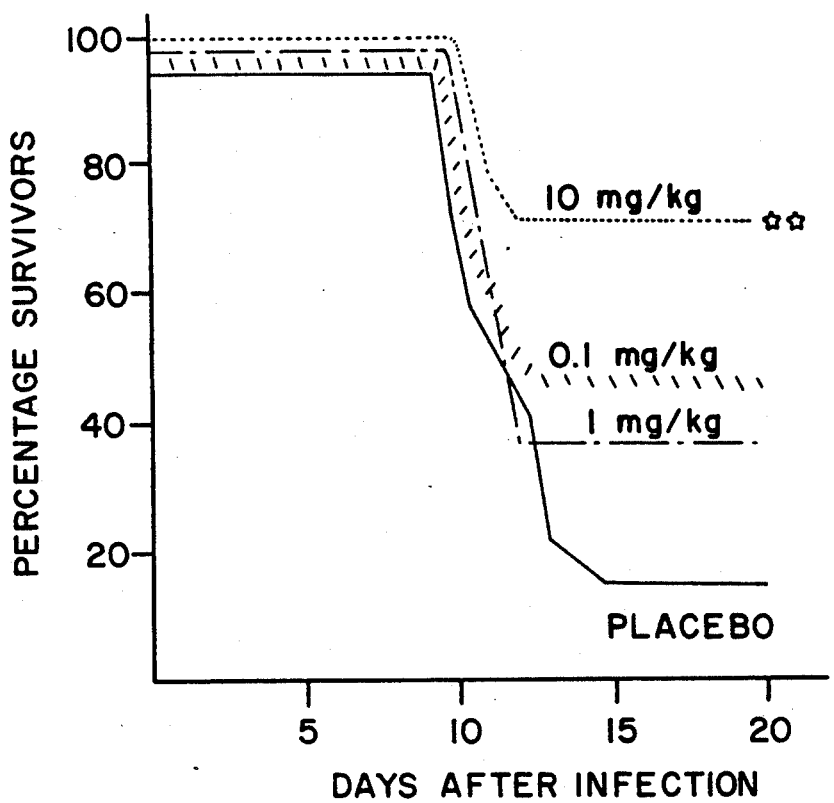
(FIG. 7a shows administration of active ingredient on 21st day before infection and FIG. 7b shows administration of active ingredient on 14th day before infection).
Figure 7B:
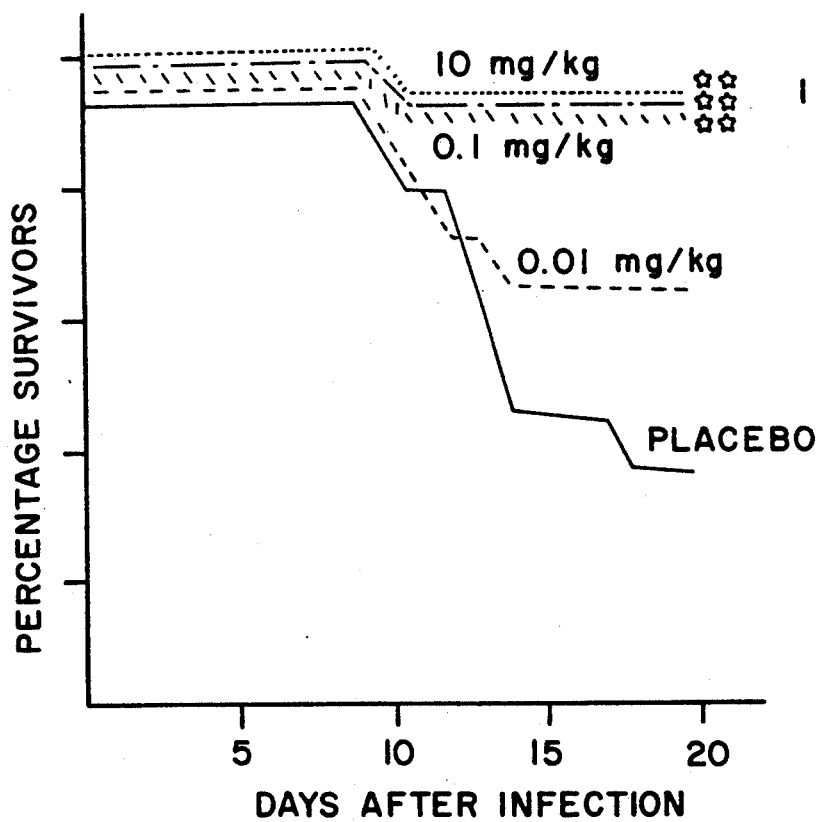
FIG. 7, Part I (FIG. 7a and FIG. 7b) shows effect of intranasally administered compound I on mice infected with Parainfluenza Virus I (Sendai)/52. Statistical significance **P≦0,01 (Vierfelder test).
(FIG. 7c shows administration of active ingredient on 7th day before infection and FIG. 7d shows administration of active ingredient on 7the day after infection).
Figure 7C:
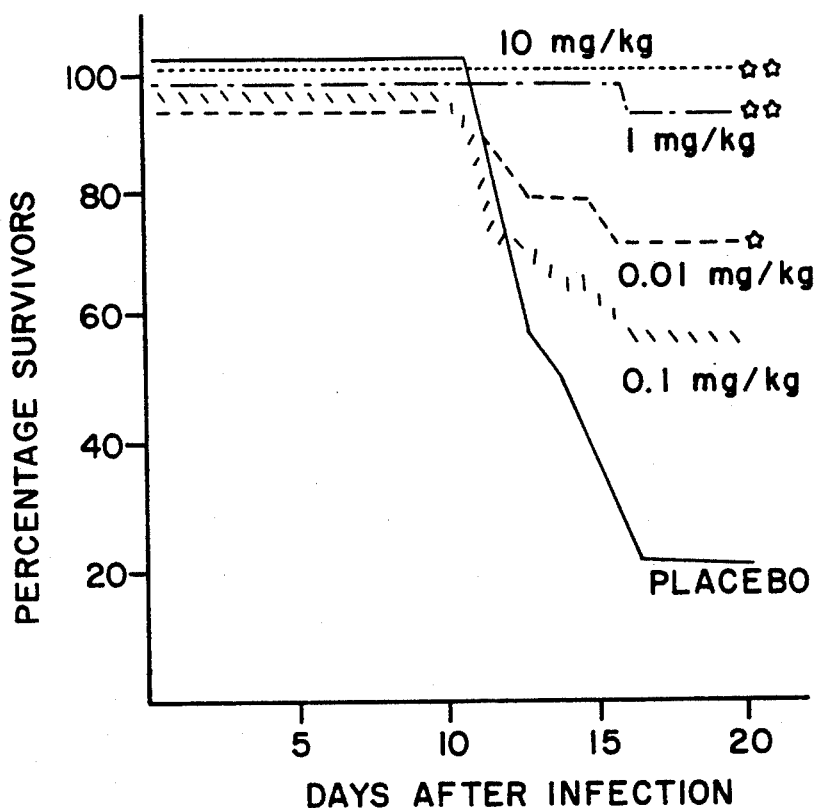
Figure 7D:
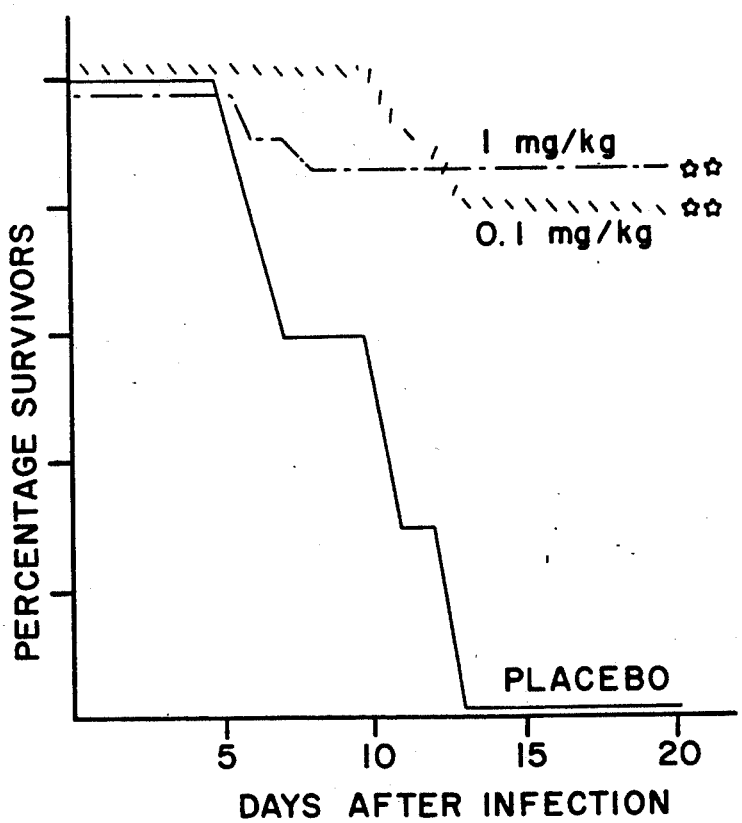

The action of compound I can be seen from FIGS. 6 and 7.

EXAMPLE 15

Groups of 30 female Tif:MF-2f (SPF) mice having a body weight of 14-16 g are infected intranasally under light anaesthesia, using a mixture of equal parts by volume of diethyl ether, ethanol and chloroform, with lethal doses (approximately $LD_{80-90}$) of the virus strains indicated in Table 4. At the time shown in Table 4 [days in relation to the day of infection] 10 of these mice in each case are administered once (single dose) with the quantity, the active ingredient, and in the manner of administration, all as indicated in Table 4.

The active ingredients are:
the sodium salt of N-acetyl-6-O-{[N-2-(1,2-dipalmitoyl-sn-glycero-3-hydroxyphosphoryloxy)-ethyl]-succinamoyl}-normuramyl-L-alanyl-D-isoglutamine (III), the sodium salt of N-acetyl-1,4,6-O-triacetylmuramyl-L-alanyl-D-isoglutaminyl-L-alanine-2-(1,2-dipalmitoyl-sn-glycero-3-hydroxyphosphoryloxy)-ethylamide (IV), the sodium salt of N-acetylmuramyl-L-alanyl-D-isoglutamine-2-(1,2-dipalmitoyl-sn-glycero-3-hydroxyphosphoryloxy)-ethylamide (V), and the sodium salt of N-acetylmuramyl-L-alanyl-D-isoglutaminyl-γ-oxymethylcarbonyl-2-(1,2-dipalmitoyl-sn-glycero-3-hydroxyphosphoryloxy)-ethylamide (VI).

The remaining 20 mice in each group serve as the control, that is to say instead of the active ingredient they receive a placebo (0.005% by weight of sodium carboxymethylcellulose in double-distilled water).

The results of the test are shown in Table 4.

EXAMPLE 16

Manufacture of 1000 tablets containing 0.5% of active ingredient

| Composition for 1000 tablets: | |
|---|---|
| compound I | 0.5 g |
| lactose, ground | 43.0 g |
| corn starch | 52.0 g |
| Pharmacoat 603 ® (hydroxypropyl-methylcellulose containing 28-30% methoxy groups, supplied by Shinetsu Chemical Company, Tokyo, Japan) | 3.0 g |
| Aerosil ® (colloidal silica, supplied by Degussa, Frankfurt, Federal Republic of Germany) | 1.0 g |
| magnesium stearate | 0.5 g |

Preparation

Compound I and 15 g of lactose are premixed. The resulting premix is mixed with 28 g of lactose and 47 g of corn starch. Using the resulting mixture and an aqueous solution of the Pharmacoat a composition suitable for granulation is prepared and is granulated, dried and ground. 5 g of corn starch, the Aerosil and magnesium stearate are mixed in and the whole is pressed to form 1000 tablets each weighing 100 mg.

The compacts can be provided with a coating that is resistant to gastric juices in a manner known per se.

EXAMPLE 17

Active ingredient in the form of a dry lyophilised substance 0.5 mg of compound I and 500 mg of mannitol (pyrogen-free) are dissolved in water for injection and sterile-filtered through a membrane filter. The sterile-filtered solution is introduced under aseptic conditions into a sterilised glass ampoule or into a glass phial and freeze-dried. After lyophilisation the ampoule is sealed or the phial is sealed with a rubber-elastomeric seal and aluminium cap.

EXAMPLE 18

Single-dose pipette with nose drops

A 0.05% solution of compound I in 1,2-propylene glycol, benzyl alcohol or ethanol or in a mixture of 1,2-propylene glycol and polyethylene glycol having an average molecular weight of 300 is prepared.

The solution is filtered and introduced into single-dose pipettes made of deformable plastics. The single-dose pipettes contain the quantity of nose drops required for one application, that is to say they each contain 0.1 ml of the above solution.

We claim:

TABLE 4

| Active ingredient | Virus | Mode of administration | Time of administration | Percentage of mice surviving 23 days after infection in dependence upon the quantity of active ingredient [mg/kg] | | | | |
|---|---|---|---|---|---|---|---|---|
| | | | | 100 | 10 | 1 | 0.1 | 0 (placebo) |
| III | Influenza A/Texas/1/77 ($H_3N_2$) | oral | +7 | | 60 | 60 | 60 | 30 |
| III | Influenza A/Texas/1/77 ($H_3N_2$) | intranasal | −7 | | | 50 | 40 | 5 |
| IV | Influenza A/Texas/1/77 ($H_3N_2$) | oral | +7 | | 50 | 40 | | 15 |
| V | Influenza A/Texas/1/77 ($H_3N_2$) | oral | +7 | 60 | 60 | 80 | | 15 |
| VI | Influenza A/Texas/1/77 ($H_3N_2$) | oral | +7 | 60 | 40 | | | 15 |

1. A method of treating a viral disease due to a virus selected from the group consisting of Herpesviridae, Poxviridae, Picornaviridae, Orthomyxoviridae and Paramyxoviridae in a warm-blooded animal in need thereof comprising administering to said animal after infection an in-vivo anti-virally effective amount of a pharmaceutically acceptable salt of a compound which is N-acetyl-muramyl-L-alanyl-D-isoglutaminyl-L-alanine-2-(1,2-dipalmitoyl-sn-glycero-3-hydroxyphosphoryloxy)-ethylamide in the absence of a vaccine.

2. The method of claim 1, wherein the sodium salt of said compound is administered as the sole active ingredient.

3. The method of claim 1, wherein said salt is administered in the form of a pharmaceutical composition containing a pharmaceutical carrier and less than 1% by weight of said salt.

4. The method of claim 1, wherein a single dose of not more than 10 mg of said salt is administered once to a warm-blooded animal of approximately 70 kg body weight.

5. The method of claim 4, wherein said dose is administered about 7 days after infection.

6. The method of claim 1 wherein a pharmaceutically acceptable salt of N-acetylmuramyl-L-alanyl-D-isoglutaminyl-L-alanine-2-(1,2-dipalmitoyl-sn-glycero-3-hydroxyphosphoryloxy)-ethylamide is administered intranasally.

7. The method of claim 1 wherein a pharmaceutically acceptable salt of N-acetylmuramyl-L-alanyl-D-isoglutaminyl-L-alanine-2-(1,2-dipalmitoyl-sn-glycero-3-hydroxyphosphoryloxy)-ethylamide is administered orally.

8. The method of claim 1 wherein said viral disease is due to a virus selected from the group consisting of Herpes simplex viruses belonging to Herpesviridae or Influenza A and Influenza B viruses belonging to Orthomyxoviridae.

9. The method of claim 1 wherein said viral disease is caused by a vaccinal virus belonging to Poxviridae, parainfluenza virus belonging to Paramyxoviridae or encephalomyocarditis virus belonging to Picornaviridae.

* * * * *